(12) United States Patent
Zhang et al.

(10) Patent No.: US 9,816,124 B2
(45) Date of Patent: Nov. 14, 2017

(54) RECOMBINANT MICROORGANISM FOR PREPARING TERPENOID AND METHOD FOR CONSTRUCTING RECOMBINANT MICROORGANISM

(71) Applicant: TIANJIN INSTITUTE OF INDUSTRIAL BIOTECHNOLOGY, CHINESE ACADEMY OF SCIENCES, Tianjin (CN)

(72) Inventors: Xueli Zhang, Tianjin (CN); Qingyan Li, Tianjin (CN); Jing Zhao, Tianjin (CN); Tao Sun, Tianjin (CN); Guanping Dai, Tianjin (CN); Hongtao Xu, Tianjin (CN); Jinlei Tang, Tianjin (CN); Yanhe Ma, Tianjin (CN)

(73) Assignee: Tianjin Institute of Industrial Biotechnology, Chinese Academy of Sciences, Tianjin (CN)

( * ) Notice: Subject to any disclaimer, the term of this patent is extended or adjusted under 35 U.S.C. 154(b) by 31 days.

(21) Appl. No.: 14/765,317

(22) PCT Filed: Jan. 28, 2014

(86) PCT No.: PCT/CN2014/000130
§ 371 (c)(1),
(2) Date: Jul. 31, 2015

(87) PCT Pub. No.: WO2014/117639
PCT Pub. Date: Aug. 7, 2014

(65) Prior Publication Data
US 2016/0068882 A1 Mar. 10, 2016

(30) Foreign Application Priority Data
Feb. 1, 2013 (CN) .......................... 2013 1 0039787

(51) Int. Cl.
*C12P 23/00* (2006.01)
*C12N 9/02* (2006.01)
*C12P 5/00* (2006.01)

(52) U.S. Cl.
CPC ............ *C12P 23/00* (2013.01); *C12N 9/0008* (2013.01); *C12P 5/007* (2013.01); *C12Y 102/04002* (2013.01)

(58) Field of Classification Search
None
See application file for complete search history.

(56) References Cited

FOREIGN PATENT DOCUMENTS

| CN | 101001947 A | 7/2007 |
| CN | 101023181 A | 8/2007 |
| CN | 101389752 A | 3/2009 |
| CN | 103087972 A | 5/2013 |

OTHER PUBLICATIONS

Darlison, M.G. et al., GenBank accession number:X0066 1.1,E.coli suc A gene for 2-oxoglutarate dehydrogenase component E1o. GenBank. database, Jul. 10, 1995.
Lu, Jiao et al., Combinatorial modulation of galP and glk gene expression for improved alternative glucose utilization, Appl Microbial Iliotechnol, vol. 93, No. 6, Dec. 13, 2011.
Zhao, Jing et al., Modulation of isoprenoid gene expression with multiple regulatory parts for improved β-carotene production. Chinese Journal of Biotechnology, vol. 29 (1), Jan. 25, 2013.
International Search Report dated May 12, 2014 for PCT/CN2014/000130.

*Primary Examiner* — Anand Desai
(74) *Attorney, Agent, or Firm* — Knobbe Martens Olson & Bear, LLP

(57) ABSTRACT

Provided are a recombinant strain for preparing a terpenoid, and method for constructing the recombinant strain. Also provided is a recombinant bacterium 1, the recombinant bacterium 1 being a recombinant bacterium obtained in order to improve the enzymatic activity of α-ketoglutarate dehydrogenase in *escherichia coli* or the mutant thereof. The method for improving the enzymatic activity of α-ketoglutarate dehydrogenase in *escherichia coli* or the mutant thereof is replacing the original regulating element of the ketoglutarate dehydrogenase gene (sucAB) in *escherichia coli* or the mutant thereof with any of the following regulating elements: artificial regulating element M 1-46, M1-37, and M1-93. Also provided are a plurality of recombinant bacteria. By improving the enzymatic activity of α-ketoglutarate dehydrogenase, succinic acid dehydrogenase and transaldolase therein and improving the ability of a cell to synthesize NADPH and ATP, the efficiency of the MEP pathway and the production capacity of terpenoid are improved.

10 Claims, 3 Drawing Sheets

SEQUENCE LISTING

```
<160> NUMBER OF SEQ ID NOS: 26

<210> SEQ ID NO 1
<211> LENGTH: 912
<212> TYPE: DNA
<213> ORGANISM: Artificial sequence
<220> FEATURE:
<223> OTHER INFORMATION: Synthetic sequence

<400> SEQUENCE: 1
atgatgacgg tctgtgcaga acaacacgtc aatttcatac acagcgatgc agccagcctg       60
ttgaacgaca ttgagcaacg gcttgatcag cttttaccgg ttgaaagcga acgtgactta      120
gtgggcgctg ccatgcgcga cggtgcgctg gcaccaggaa agcgtatccg tccactgctg      180
ttgttgctgg cagcgcgcga tctgggctgc aacgccacgc ctgccggcct gcttgatctc      240
gcctgcgcgg tagagatggt gcatgccgca tcactgattc tggatgacat gccctgcatg      300
gatgatgcgc aactgcgtcg cggacgtccg accattcatt gccagtatgg tgaacatgtc      360
gcgattctgg ccgcggtggc cctgctgagt aaggcattcg gcgtggtcgc tgcggcagaa      420
ggcttaacgg caaccgccag agccgacgct gtagcagaat tatcccacgc agtcggcatg      480 cagggggctgg tgcagggggca gtttaaggat ctctccgaag gtgacaagcc acgcagcgct      540
gacgccattc tgatgaccaa tcactataaa accagcaccc tgttctgcgc ctccatgcag      600
atggcttcta tcgtggctga agcctcaggt gaagcccgcg aacagctgca ccgttttcg      660 cttaatcttg gtcaggcttt ccagctactg gacgatctca ctgacggcat ggccgacacc      720
ggtaaagatg cccatcagga tgacgggaaa tcaacgctgt gaatctgct ggggccacag      780 gcggttgaaa cgcgactgcg cgatcatctg cgctgcgcca gcgagcatct gttatcggcc      840
```

| | |
|---|---:|
| tgccaggacg gttatgccac acaccatttt gttcaggcct ggtttgagaa aaaactcgct | 900 |
| gccgtcagtt aa | 912 |

<210> SEQ ID NO 2
<211> LENGTH: 1295
<212> TYPE: DNA
<213> ORGANISM: Artificial sequence
<220> FEATURE:
<223> OTHER INFORMATION: Synthetic sequence

<400> SEQUENCE: 2

| | |
|---|---:|
| atgagccact tgcggtcat tgcaccgccc ttctatagcc atgtgcaggc gcttcagcac | 60 |
| cttagccagg ccttaatcgc acgcggacac cagatcactt tcatccagca gacggacgtt | 120 |
| agcgcgctac tcaccgatag ccgtatcggc ttttcccgc tgggtttagc ctcgcatccg | 180 |
| gcgggcagtc tggcacacac cctgcaactg gcggcgcacc ctctcggccc ctcaatgctg | 240 |
| aaactgatca atgagatggc ccgcagcacc gatatgctct gtcgtgaact gcccgtggtg | 300 |
| ctgagcacgc tggcgattga tggcgtgatc gtcgatcaga tggagcctgc cggtgcactg | 360 |
| gcggcagaag cgctgaacct gccttatgtt tcggttgcct gtgcgctgcc acttaaccgt | 420 |
| gaagcggatt cccgctggc cgtgatgccg tttgactatg ccaggaccga tcaggcgcgc | 480 |
| gaacgctatc gcaccagtga aaaaatctat gactggctga tgcgacgtca cgatcgggtg | 540 |
| atcgcccgca acgctcatgc gatgggatta gcgccacggg aaaaactgca tcactgtttt | 600 |
| tcaccgctgg cgcagatcag ccagctgatt ccggaactgg attttccccg ccaggcgttg | 660 |
| cccgatcatt tccattcggt tggcccgctg cgtaccactg aaccggcacc cgccgcgtcg | 720 |
| cagcctcgct acttcccgca tgatgacaaa ccgcgcattt ttgcttccct cggcacgctg | 780 |
| cagggacatc gctacggcct gttttaaaacc atcgtccgcg cctgccagga gctcgatgct | 840 |
| cagttattgc tggcgcattg cggtcggttg tcacctttcc aggcggagaa actggcgcag | 900 |
| gccagccatg ttcaggtggt cgattttgcc gaccaggcag ctgcactggc tcaggccgat | 960 |
| cttgccatta cgcacggcgg catgaatacg gtgctggatg ggattaacca cctgacgccg | 1020 |
| ctgctgacga tcccgctggc ctttgatcag ccgggtgtgg ctgccagagt ggtctggcac | 1080 |
| ggtatcggac gtcgcgcctc acgcttcacc accagccact ccatggcgcg tcagctccag | 1140 |
| accttactgg ctgatgaaag ctacgttcag cagatgaaaa cgctgcgtag cgcacttcgt | 1200 |
| caggcgggcg gaaccaccct ggcggcggac attgtcgaac aggcgatgct gacccgccag | 1260 |
| ccggtcctca ccaggagaga ctatgccgcg gtatg | 1295 |

<210> SEQ ID NO 3
<211> LENGTH: 1151
<212> TYPE: DNA
<213> ORGANISM: Artificial sequence
<220> FEATURE:
<223> OTHER INFORMATION: Synthetic sequence

<400> SEQUENCE: 3

| | |
|---|---:|
| atgatctgat tctggtgggc gcgggactgg ccaacgggct gatcgccctg cgcctgagac | 60 |
| agcagcggcc ctccctgcgc attctgctga ttgacgccga acgtgaaccg ggtgccaatc | 120 |
| atacctggtc gtttcatgcg gaagatctca ccgaaacgca gcatcgctgg atcgctccgc | 180 |
| tggtagtaca tcactggcct ggctatgagg tccgctttcc ccaacgcagt cgtagtctga | 240 |
| acagtggcta ttttgcgtg acttcggagc gcttcgtgca ggtcatccgc gacaggtttg | 300 |

| | |
|---|---|
| cgccggatct gctgctgaat acccgggttg cgggcatcgc ttcacgcacg gttacgctgg | 360 |
| acgatggccg ggtgctggag agtgacgcag tgattgatgg ccgtggctac cagcccgatg | 420 |
| ccgcgctgtg catgggcttc cagtcgtttg tcggacagga gtggcagctc agcgagccac | 480 |
| atggcctgac cgcgccgatc atcatggatg ccacggtaga tcagcaggca ggctatcgct | 540 |
| tgtctacag cctgcccttt tctgcagaca ccctgctgat tgaagatacc cactacattg | 600 |
| ataacgccac gctggaaggc gatcgcgccc gtcagaatat ccgcgcctat gccgcgcagc | 660 |
| aggggtggcg gttagaccga ctgctacgcg aagagcaagg cgcgttaccc attacgctga | 720 |
| ccggcgacgt ggccgccttc tggcagaaac acgatctgcc ctgcagcggt ttgcgtgccg | 780 |
| ggttattcca tccgactacc ggctattctc tgccgctggc ggtcgcgctg gctgaccggc | 840 |
| tggcgcagat gcagacgttt acctctgaga ccctgcacgc caccattcag caattcgcca | 900 |
| gtcaggcctg gcagcaacag cgcttcttcc gcatgctgaa ccgtatgctg tttctggcgg | 960 |
| gtccggctga ccagcgctgg caggttatgc aacgttttta cggccttccc gaaggtctga | 1020 |
| tcgcccgttt ttatgcggga aaactcactt tgcctgatcg gctgcgcatc ttaagcggca | 1080 |
| agccccggt ccccgttctg gcggcgttac aggctattat gactcctcac cgtcaacagg | 1140 |
| cgatgcaatg a | 1151 |

<210> SEQ ID NO 4
<211> LENGTH: 1479
<212> TYPE: DNA
<213> ORGANISM: Artificial sequence
<220> FEATURE:
<223> OTHER INFORMATION: Synthetic sequence

<400> SEQUENCE: 4

| | |
|---|---|
| atgaatagaa ctacagtaat tggcgcaggc tttggtggtc tggctctggc cattcgcctt | 60 |
| caggcgtcag gcgttcccac ccgactgctg agcagcgtg acaagccggg cggccgggct | 120 |
| tatgtctatc aggatcaggg cttcacgttt gatgccggcc ccacggtaat caccgatccc | 180 |
| agcgccattg aagagctgtt cactctggcg ggtaaaaagc tctctgacta tgtcgagctg | 240 |
| atgccggtga gccgttttta cgcctctgc tgggagtccg gcaaggtgtt cagttatgac | 300 |
| aacgatcagc ccgcgctgga agcgcagatt gccgcattta atccgcgtga cgttgaagga | 360 |
| tatcggcgct ttctggccta ttcccgagcg gtgtttgctg aaggctatct gaagcttggc | 420 |
| accgtgccgt ttctgtcatt ccgcgacatg ctgcgggccg cgcctcagct ggcaaaactt | 480 |
| caggcatggc gcagcgttta cagcaaagtg gcgagctaca ttgaagatga gcatctgcgt | 540 |
| caggccttct ctttccactc actgctggtg ggcggaaatc cgtttgccac ttcctcaatc | 600 |
| tatacccctga ttcatgcgct ggaacgtgaa tggggcgtct ggttcccgcg cggtggcacg | 660 |
| ggcgcgctgg tgcagggcat ggtgaaactg tttgaagatc tgggcggcga agtggagctc | 720 |
| aatgccagcg ttgcccggct ggagacccag gaaaacagga ttaccgcggt gcacctgaaa | 780 |
| gatggccggg tcttcccgac ccgcgcggtt gcctccaacg cagatgtggt tcacacctac | 840 |
| cgcgaactgc tgagccagca ccccgcttcg caggcgcagg acggtcact gcagaacaaa | 900 |
| cgcatgagta actcgctgtt tgtgatctat tttggcctga atcatcatca cgatcagctg | 960 |
| gcgcaccaca cggtctgctt tggtccgcgc tatcgtgagt tgattgatga aatctttaac | 1020 |
| aaagatggcc tggcagagga cttctcgctc tatctgcatg cgccctgcgt gaccgatccc | 1080 |
| tcactggcac cggaaggctg cggcagctac tacgtgctgg cgccggtacc gcacctcggc | 1140 |
| accgctgata tcgactgggc cgttgaaggt ccgcgcctgc gcgatcgcat tttcgactat | 1200 |

```
ctggaacagc attacatgcc gggcctgcgt agccagttgg tcacgcatcg catcttcacg    1260
ccgtttgatt tccgcgatga gctgaatgcg tatcagggct cggccttctc agtggagcca    1320
atcctgacgc aaagcgcctg gttccggcct cacaaccgcg ataaaaatat taataatctc    1380
tatctggtcg gtgctggtac ccatcctggc gcgggtattc caggggtgat tggctcggcc    1440
aaggctaccg caggattgat gctggaggat ctggcttga                          1479
```

<210> SEQ ID NO 5
<211> LENGTH: 891
<212> TYPE: DNA
<213> ORGANISM: Artificial sequence
<220> FEATURE:
<223> OTHER INFORMATION: Synthetic sequence

<400> SEQUENCE: 5

```
atggaggtgg gatcgaaaag ctttgccacc gcgtcaaaac tgtttgatgc caaacccga     60 cgcagcgtgc tgatgctcta cgcctggtgc cgtcactgtg atgatgtgat tgacgatcag    120
gtcctgggat tcagcaacga tacgccatcg ctgcaatctg ccgaacagcg cctggcgcag    180
ctggagatga aaacgcgtca ggcctatgcc ggatcccaga tgcatgagcc cgcctttgcg    240
gcctttcagg aggtggcaat ggcgcacgat attctgcctg cttacgcttt tgatcatctg    300
gcgggctttg cgatggacgt gcatgagaca cgctatcaga cgctggatga tacgctgcgt    360
tactgttacc acgtcgcggg cgtggttggc ctgatgatgg cgcagattat gggcgtacgc    420
gacaacgcca cgctggatcg cgcctgcgat tcggtctggg cgtttcagct gaccaatatt    480
gcgcgcgata tcgttgaaga tgctgaagcg ggacgctgct atctgcccgc tgcgtggctg    540
gctgaagagg ggctgacccg agagaatctc gccgatccgc aaaatcgcaa ggcattaagc    600
cgcgtcgccc gtcggctggt ggaaacggcg gagccctatt atcgatcggc gtcggctggc    660
ctgccgggtt taccgctgcg ttcagcgtgg gcgattgcta ccgcgcagca ggtctatcgt    720
aaaatcggta tgaaggtggt tcaggcgggt tcacaggcgt gggagcaacg ccagtccacc    780
agcacgccag agaaactggc actgctggtg gcggcatcgg tcaggcggt tacttcccgg    840 gtggcgcgtc acgctccacg ctcagctgat ctctggcagc gccccgttta a             891
```

<210> SEQ ID NO 6
<211> LENGTH: 249
<212> TYPE: DNA
<213> ORGANISM: Artificial sequence
<220> FEATURE:
<223> OTHER INFORMATION: Synthetic sequence

<400> SEQUENCE: 6

```
cgactgcacg gtgcaccaat gcttctggcg tcaggcagcc atcggaagct gtggtatggc     60
tgtgcaggtc gtaaatcact gcataattcg tgtcgctcaa ggcgcactcc cgttctggat    120
aatgtttttt gcgccgacat cataacggtt ctggcaaata ttctgaaatg agctgttgac    180
aattaatcat ccggctcgta taatgtgtgg aattgtgagc ggataacaat ttcacacagg    240
aaacagacc                                                            249
```

<210> SEQ ID NO 7
<211> LENGTH: 100
<212> TYPE: DNA
<213> ORGANISM: Artificial sequence
<220> FEATURE:
<223> OTHER INFORMATION: Synthetic sequence -continued

```
<400> SEQUENCE: 7
ttatctctgg cggtgttgac aagagataac aacgttgata taattgagcc cttttggtgc    60
gtcagtcagt ttaaaccagg aaacagctat gaccatgatt                         100

<210> SEQ ID NO 8
<211> LENGTH: 30
<212> TYPE: DNA
<213> ORGANISM: Artificial sequence
<220> FEATURE:
<223> OTHER INFORMATION: Synthetic sequence

<400> SEQUENCE: 8
gcgaaaaata ttgagagtca gacattcatt                                     30

<210> SEQ ID NO 9
<211> LENGTH: 100
<212> TYPE: DNA
<213> ORGANISM: Artificial sequence
<220> FEATURE:
<223> OTHER INFORMATION: Synthetic sequence

<400> SEQUENCE: 9
ttatctctgg cggtgttgac aagagataac aacgttgata taattgagcc cgtgttttcc    60
catgaaaagt ttaaaccagg aaacagctat gaccatgatt                         100

<210> SEQ ID NO 10
<211> LENGTH: 100
<212> TYPE: DNA
<213> ORGANISM: Artificial sequence
<220> FEATURE:
<223> OTHER INFORMATION: Synthetic sequence

<400> SEQUENCE: 10
ttatctctgg cggtgttgac aagagataac aacgttgata taattgagcc actggctcgt    60
aatttattgt ttaaaccagg aaacagctat gaccatgatt                         100

<210> SEQ ID NO 11
<211> LENGTH: 100
<212> TYPE: DNA
<213> ORGANISM: Artificial sequence
<220> FEATURE:
<223> OTHER INFORMATION: Synthetic sequence

<400> SEQUENCE: 11
ttatctctgg cggtgttgac aagagataac aacgttgata taattgagcc cgtattgtta    60
gcatgtacgt ttaaaccagg aaacagctat gaccatgatt                         100

<210> SEQ ID NO 12
<211> LENGTH: 127
<212> TYPE: DNA
<213> ORGANISM: Artificial sequence
<220> FEATURE:
<223> OTHER INFORMATION: Synthetic sequence

<400> SEQUENCE: 12
tttaaatggt ttttacctgt cggcatccgc tcaaaacggg cggttgtcga taaacgctca    60
cttggttaat catttcactc ttcaattatc tataatgatg agtgatcaga attacatgtg   120
agaaatt                                                             127

<210> SEQ ID NO 13
<211> LENGTH: 100
```

```
<212> TYPE: DNA
<213> ORGANISM: Artificial sequence
<220> FEATURE:
<223> OTHER INFORMATION: Synthetic sequence

<400> SEQUENCE: 13
ttatctctgg cggtgttgac aagagataac aacgttgata taattgagcc tgaggtggct     60
tattattcgt ttaaaccagg aaacagctat gaccatgatt                          100

<210> SEQ ID NO 14
<211> LENGTH: 100
<212> TYPE: DNA
<213> ORGANISM: Artificial sequence
<220> FEATURE:
<223> OTHER INFORMATION: Synthetic sequence

<400> SEQUENCE: 14
ttatctctgg cggtgttgac aagagataac aacgttgata taattgagcc tctcgcccca     60
ccaattcggt ttaaaccagg aaacagctat gaccatgatt                          100

<210> SEQ ID NO 15
<211> LENGTH: 85
<212> TYPE: DNA
<213> ORGANISM: Artificial sequence
<220> FEATURE:
<223> OTHER INFORMATION: Synthetic sequence

<400> SEQUENCE: 15
cgtaacaaag aaatgcagga aatctttaaa aactgcccct gacactaaga cagttttttaa    60 aggttccttc gcgagccact acgta                                           85

<210> SEQ ID NO 16
<211> LENGTH: 156
<212> TYPE: DNA
<213> ORGANISM: Artificial sequence
<220> FEATURE:
<223> OTHER INFORMATION: Synthetic sequence

<400> SEQUENCE: 16
catccttacc gctctggcgt atcacgtcgt cgtaggtatt cgccacatga tgatggattt     60
tggctatctg gaagaaacat tcgaagcggg taaacgctcc gccaaaatct cctttgttat   120
tactgtcgtg ctttcacttc tcgcaggagt cctcgt                             156

<210> SEQ ID NO 17
<211> LENGTH: 47
<212> TYPE: DNA
<213> ORGANISM: Artificial sequence
<220> FEATURE:
<223> OTHER INFORMATION: Synthetic sequence

<400> SEQUENCE: 17
agaccggtta catcccccta acaagctgtt taaagagaaa tactatc                  47

<210> SEQ ID NO 18
<211> LENGTH: 299
<212> TYPE: DNA
<213> ORGANISM: Artificial sequence
<220> FEATURE:
<223> OTHER INFORMATION: Synthetic sequence

<400> SEQUENCE: 18
tgaagtcggt atttcaccta agattaactt atgtaacagt gtggaagtat tgaccaattc     60
```

```
attcgggaca gttattagtg gtagacaagt ttaataattc ggattgctaa gtacttgatt       120
cgccatttat tcgtcatcaa tggatccttt acctgcaagc gcccagagct ctgtacccag       180
gttttcccct ctttcacaga gcggcgagcc aaataaaaaa cgggtaaagc caggttgatg       240
tgcgaaggca aatttaagtt ccggcagtct tacgcaataa ggcgctaagg agaccttaa       299
```

<210> SEQ ID NO 19
<211> LENGTH: 50
<212> TYPE: DNA
<213> ORGANISM: Artificial sequence
<220> FEATURE:
<223> OTHER INFORMATION: Synthetic sequence

<400> SEQUENCE: 19

```
tcaccctgaa gagaatcagg gcttcgcaac cctgtcatta aggaggagct                  50
```

<210> SEQ ID NO 20
<211> LENGTH: 162
<212> TYPE: DNA
<213> ORGANISM: Artificial sequence
<220> FEATURE:
<223> OTHER INFORMATION: Synthetic sequence

<400> SEQUENCE: 20

```
ataacgcgca tctttcatga cggcaaacaa tagggtagta ttgacaagcc aattacaaat       60
cattaacaaa aaattgctct aaagcatccg tatcgcagga cgcaaacgca tatgcaacgt      120
ggtggcagac gagcaaacca gtagcgctcg aaggagaggt ga                         162
```

<210> SEQ ID NO 21
<211> LENGTH: 85
<212> TYPE: DNA
<213> ORGANISM: Artificial sequence
<220> FEATURE:
<223> OTHER INFORMATION: Synthetic sequence

<400> SEQUENCE: 21

```
cgtaacaaag aaatgcagga atctttaaa aactgcccct gacactaaga cagtttttaa        60
aggttccttc gcgagccact acgta                                             85
```

<210> SEQ ID NO 22
<211> LENGTH: 63
<212> TYPE: DNA
<213> ORGANISM: Artificial sequence
<220> FEATURE:
<223> OTHER INFORMATION: Synthetic sequence

<400> SEQUENCE: 22

```
tttaacaggg caacggaaca cccgcccaga gcataaccaa accaggcagt aagtgagaga       60
aca                                                                     63
```

<210> SEQ ID NO 23
<211> LENGTH: 121
<212> TYPE: DNA
<213> ORGANISM: Artificial sequence
<220> FEATURE:
<223> OTHER INFORMATION: Synthetic sequence

<400> SEQUENCE: 23

```
gttttttac atggcacgaa agaccaaaca tttgttatca aatggtaaat aataagtgag        60
ctaaaagttg cttaacgaaa gcaaaacaga aagaaaaaat taatcaggtg aggagcaggt      120
c                                                                      121
```

<210> SEQ ID NO 24
<211> LENGTH: 202
<212> TYPE: DNA
<213> ORGANISM: Artificial sequence
<220> FEATURE:
<223> OTHER INFORMATION: Synthetic sequence

<400> SEQUENCE: 24

```
ctgttggaat gttgcgctaa tgcataagcg actgttaatt acgtaagtta ggttcctgat      60
tacggcaatt aaatgcataa acgctaaact tgcgtgacta cacattcttg agatgtggtc     120
attgtaaacg gcaattttgt ggattaaggt cgcggcagcg gagcaacata tcttagttta     180
tcaatataat aaggagttta gg                                              202
```

<210> SEQ ID NO 25
<211> LENGTH: 62
<212> TYPE: DNA
<213> ORGANISM: Artificial sequence
<220> FEATURE:
<223> OTHER INFORMATION: Synthetic sequence

<400> SEQUENCE: 25

```
gtaagaaaat tacaagtata ccctggctta agtaccgggt tagttaactt aaggagaatg      60
ac                                                                     62
```

<210> SEQ ID NO 26
<211> LENGTH: 72
<212> TYPE: DNA
<213> ORGANISM: Artificial sequence
<220> FEATURE:
<223> OTHER INFORMATION: Synthetic sequence

<400> SEQUENCE: 26

```
ccggcgtagc ccaaaacgcg ctgtcgtcaa gtcgttaagg gcgtgccctt catcatccga      60
tctggagtca aa                                                          72
```

RECOMBINANT MICROORGANISM FOR PREPARING TERPENOID AND METHOD FOR CONSTRUCTING RECOMBINANT MICROORGANISM

CROSS REFERENCE TO RELATED APPLICATIONS

This application is the U.S. National Phase of International Application No. PCT/CN2014/000130 filed Jan. 28, 2014, designating the U.S. and published in Chinese as WO 2014/117639 A1 on Aug. 7, 2014 which claims the benefit of Chinese Patent Application No. 201310039787.8, filed Feb. 1, 2013.

FIELD OF THE INVENTION

The present invention relates to biotechnical filed, and particularly to a recombinant strain for producing a terpenoid and a method for constructing the same.

BACKGROUND

Terpenoids widely exist in higher plants, fungi, microorganisms, insects, and marine organisms in nature. More than 50 thousands of terpenoids have been discovered by now, most of which are biologically active ingredients in medicaments and health care products, for example, monoterpenes (C1O): Menthol, Linalool; sesquiterpenes (C15): Artemissinin; diterpenes (C20): Taxol, Tanshinone 11A; triterpenes (C30): Ginsenosides, Notoginsenosides, Glycyrrhizine; tetraterpenes (C40): Lycopene, β-carotene, Zeaxanthin, Cathaxanthin, and Astaxanthin, Carotenoides etc.; polyterpenes: Coenzyme Q10; terpenoid alkaloid: Dendrobine, Gentianine, Aconitine, Reserpine, and the like.

In view of that terpenoids are promising in a wide range of uses and have a great market demand, the methods for effectively producing terpenoids are always hot spots of present research. Currently, there are mainly three methods for producing terpenoids: chemical synthesis, plant extraction, and microorganism fermentation. Chemical synthesis has a complex process, high energy consumption, and severe pollution; on the other hand, terpenoids are often at a low amount in plants, and extraction from plant may cause serious damage to wild plant resource; in contrast, microorganism fermentation may be greatly advantageous due to no restriction from raw materials and being a friendly and clean production process.

There are two types of microorganism fermentation, and one of them uses wild strains. However, only a few of wild-type microorganism strains can produce terpenoids at present, and have relatively low productability of fermentation. Although traditional mutagenesis breeding may improve strain fermentation ability to some extent, it is more random, and less effective, and results in unstable mutant strain. The other one is fermentation using constructed recombinant strains. As continuous development in metabolic engineering and synthetic biological technology recently, more types of terpenoids are synthesized with recombinant strains in higher yield. The most commonly used recombinant strain is Escherichia coli (E. coli). In many studies, E. coli is selected as a starting strain for engineering because its genome sequence has been fully disclosed, it is clear in terms of genetic background and metabolic pathway, and it has many advantages such as simple demand for medium and fast growth (Ajikumar et al., 2008; Das et al., 2007; Keasling, 2008; Lee et al., 2002).

β-carotene and lycopene are two typical types of terpenoids. β-carotene has effects of antioxidation, detoxification, anticancer, preventing cardiovascular diseases, preventing and treating cataract, protecting liver, and the like. Moreover, β-carotene is also called "source of Vitamin A", which is an important physiological function active substance in human, and is capable of treating epithelial cell keratinization, ophthalmoxerosis, nyctalopia, etc., caused by lack of Vitamin A (Lee et al., 2002; Das et al., 2007). Lycopene is the main constituent of red pigments of tomato, and is an excellent antioxidant. Lycopene is capable of preventing human tissues and organs from damage by a metabolic product of "free radical", and may be used in natural heath foods or drugs. Lycopene-containing health foods are capable of preventing age-related deterioration of eyesight, resisting aging, and preventing cardiovascular diseases, and also exert some inhibition to each of digestive tract, cervical, breast, skin, bladder cancers and the like. Lycopene is nontoxic and harmless, and may be added to food such as ice cream, fruit syrup, hard candy, bread, cookie, cake, etc., like β-carotene, so as to improve the nutritional value thereof. It is superior to Vitamin E and β-carotene in health care effect.

Many natural microorganism, e.g., *Blakeslea trispora, Pantoea agglomerans, Phaffia rhodozyma*, etc., can synthesize β-carotene and lycopene (Mehta et al., 2003). DMAPP is successively react with 2 molecules of IPP, under the action of farnesyl diphosphate (FPP) synthase, to form FPP; FPP and IPP react, under the action of geranyl-geranyl diphosphate (GGPP) synthase, to form GGPP. Phytoene is synthesized head-to-head from 2 molecules of GGPP under the action of phytoene synthase (CrtB); lycopene is formed from phytoene under the action of phytoene desaturase (CrtI); and β-carotene is formed from lycopene under the action of β-lycopene cyclase (crtY).

Isopentenyl pyrophosphate (IPP) and dimethylallyl pyrophosphate (DMAPP) are precursor compounds of all terpenoid compounds. There are two synthetic pathways known so far (Lee et al., 2002). One is Mevalonic Acid Pathway (MVA pathway), mainly found on cytosol or endoplasmic reticulum in fungi and plants. Through this pathway, three molecules of acetyl coenzyme A are condensed to form 3-hydroxy-3-methyl-glutaryl coenzyme A (HMG-COA), and subjected to a two-step kinase reaction to form mevalonate pyrophosphate (MVA), and finally subjected to multi-step phosphorylation and decarboxylation reactions to produce IPP. The other one is MEP pathway, mainly found in bacteria, green alga and plant plasmids. This pathway is started with a starting material of 3-phosphoglyceraldehyde and pyruvic acid, and catalyzed with 1-deoxy-D-xylulose-5-phosphate synthase (Dxs) and 1-deoxy-D-xylulose-5-phosphate reductoisomerase (Dxr) to form 2-C-methyl-D-erythritol-4-phosphate (MEP). MEP is then formed into 2-C-methyl-D-erythritol-2,4-cyclodiphosphate (MEC), through three successive reactions catalyzed by 4-diphosphocytidy 1-2C-methyl-D-erythritol synthase (IspD), 4-diphosphocytidyl-2-C-methyl erythritol kinase (IspE) and 2C-methyl-D-erythritol 2,4-cyclodiphosphate synthase (IspF). MEC is then is formed into (E)-4-hydroxy-3-methyl-2-butenyl-diphosphate (HMBPP) under the action of (E)-4-hydroxy-2-methyl-2-butenyl4-diphosphate synthase (IspG). Next, HMBPP is catalyzed with HMBPP reductase (1-hydroxy-2-methyl-2-(E)-butenyl-4-diphosphate reductase, IspH) to form a mixture of IPP and DMAPP of 5:1. IPP is catalyzed with isopentenyl diphosphate isomerase (Idi) to be isomerized into dimethyl allyl pyrophosphate, DMAPP. IPP and DMAPP are basic C5 units of terpenoids, based on which various terpenoids may be synthesized.

In order for production of a terpenoid from *E. coli*, it is first necessary to introduce genes for synthesizing the terpenoid into *E. coli*. However, due to poor ability of *E. coli* to synthesize IPP and DMAPP, it always leads to a low terpenoid production. For improving the ability of synthesizing terpenoid by recombinant *E. coli*, it is required to enhance the ability to synthesize IPP and DMAPP thereof. Currently, there are mainly two solutions for enhancing the ability of recombinant *E. coli* to synthesize IPP and DMAPP: one being to introduce a foreign MVA pathway (e.g., the MVA pathway from *Saccharomyces cerevisiae*) (Martin et al., 2003; Yoon et al., 2007; Yoon et al., 2009); the other one being to improve the efficiency of *E. coli* own MEP pathway by increasing the expression strength of a key gene in MEP pathway and increasing supplies of precursor compounds of MEP pathway, 3-phosphoglyceraldehyde and pyruvic acid (Ajikumar et al., 2010; Alper et al., 2005a; Alper et al., 2005b; Choi et al., 2010; Jin and Stephanopoulos, 2007; Yuan et al., 2006).

In increasing the expression strength of a key gene in MEP pathway, previous attempts all focused on use of strong promoters (such as T5 promoter) (Yuan et al., 2006). Studies show that overexpression of 1-deoxy-D-xylulose-5-phosphate synthase gene (dxs), 4-diphosphocytidyl-2C-methyl-D-erythritol synthase gene (ispD) and 4-diphosphocytidyl-2-C-methyl-D-erythritol kinase gene (ispF), 2-C-methyl-D-erythritol-2,4-cyclopyrophosphate synthase gene (ispE), isopentenyl diphosphate isomerase gene (idi) in MEP pathway can improve the ability of *E. coli* in production of β-carotene. However, increase in the expression intensities of 1-deoxy-D-xylulose-5-phosphate reductoisomerase gene (dxr), 1-hydroxy-2-methyl-2-(E)-butenyl-4-diphosphate synthase gene (ispG), 1-hydroxy-2-methyl-2-(E)-butenyl-4-diphosphate reductase gene (ispH) in MEP pathway reduces the ability of recombinant *E. coli* in production of β-carotene (Yuan et al., 2006).

In another aspect, nicotinamide adenine dinucleotide phosphate (NADPH) and adenosine triphosphate (ATP) are key cofactors in MEP pathway. Insufficient supply of the cofactors will result in low efficiency in MEP pathway.

SUMMARY OF THE INVENTION

An object of the present invention is to provide a recombinant strain 1.

The present invention provides a recombinant strain 1 that is constructed by a method comprising a step of: improving the enzymatic activity of α-ketoglutarate dehydrogenase in *E. coli* or in its mutant to obtain the recombinant strain 1.

In above recombinant strain 1, the method for improving the enzymatic activity of α-ketoglutarate dehydrogenase in *E. coli* or a mutant thereof is replacing original regulatory part of α-ketoglutarate dehydrogenase gene, sucAB, in *E. coli* or a mutant thereof with any of following regulatory parts: artificial regulatory parts M1-46, M1-37 and M1-93;

Said artificial regulatory part M1-46 has a nucleotide sequence of SEQ ID NO: 14 in the sequence listing;

Said artificial regulatory part M1-37 has a nucleotide sequence of SEQ ID NO: 10 in the sequence listing;

Said artificial regulatory part M1-93 has a nucleotide sequence of SEQ ID NO: 11 in the sequence listing;

Said regulatory part of α-ketoglutarate dehydrogenase gene, sucAB, has a sequence of SEQ ID NO: 15 in the sequence listing.

Above recombinant strain 1 is recombinant strain 1-1 or recombinant strain 1-2 or recombinant strain 1-3:

Above recombinant strain 1-1 is to improve the enzymatic activity of α-ketoglutarate dehydrogenase in *E. coli*; the improvement of the enzymatic activity of α-ketoglutarate dehydrogenase in *E. coli* is achieved particularly by replacing original regulatory part of α-ketoglutarate dehydrogenase gene, sucAB, in *E. coli* with artificial regulatory part M1-46; particularly by way of homologous recombination; see Example 16, I.1 for details.

Above recombinant strain 1-2 is to improve the enzymatic activity of α-ketoglutarate dehydrogenase in *E. coli* mutant A; the improvement of the enzymatic activity of α-ketoglutarate dehydrogenase in *E. coli* mutant A is achieved particularly by replacing original regulatory part of α-ketoglutarate dehydrogenase gene sucAB in *E. coli* mutant A with any of following regulatory parts: artificial regulatory parts M1-46, M1-37 and M1-93;

Above replacement of original regulatory part of α-ketoglutarate dehydrogenase gene sucAB in *E. coli* mutant A (CAR001) with artificial regulatory part M1-46 results in SucAB46-FKF; particularly by way of homologous recombination, as seen in Example 3, part 1.

Above replacement of original regulatory part of α-ketoglutarate dehydrogenase gene sucAB in *E. coli* mutant CAR001 with artificial regulatory part M1-37 results in SucAB37-FKF; particularly by way of homologous recombination, as seen in Example 3, part 1.

Above replacement of original regulatory part of α-ketoglutarate dehydrogenase gene sucAB in *E. coli* mutant CAR001 with artificial regulatory part M1-93 results in SucAB93-FKF; particularly by way of homologous recombination, as seen in Example 3, part 1.

The *E. coli* mutant A (CAR001) is constructed by a method comprising steps of (see Example 2 for details):

1) introducing a β-carotene synthesis gene cluster and a trc regulatory part into *E. coli*, to obtain recombinant *E. coli* (QL002);

2) replacing trc regulatory part of β-carotene synthesis gene cluster, the original regulatory part of 1-deoxy-D-xylulose-5-phosphate synthase gene dxs and the original regulatory part of isopentenyl diphosphate isomerase gene idi in recombinant *E. coli* as below to obtain *E. coli* mutant A (CAR001):

replacing trc regulatory part of β-carotene synthesis gene cluster with artificial regulatory part M1-93;

replacing original regulatory part of 1-deoxy-D-xylulose-5-phosphate synthase gene with artificial regulatory part M1-37;

replacing original regulatory part of isopentenyl diphosphate isomerase gene, idi, with artificial regulatory part M1-46;

above replacements of trc regulatory part of β-carotene synthesis gene cluster, original regulatory part of 1-deoxy-D-xylulose-5-phosphate synthase gene dxs and original regulatory part of isopentenyl diphosphate isomerase gene idi in recombinant *E. coli* are performed particularly in an order of steps of:

1) replacing trc regulatory part of β-carotene synthesis gene cluster with artificial regulatory part M1-12, to obtain QL105;

2) replacing original regulatory part of 1-deoxy-D-xylulose-5-phosphate synthase gene dxs in QL105 with artificial regulatory part M1-37, to obtain Dxs37;

3) replacing original regulatory part of isopentenyl diphosphate isomerase gene idi in Dxs37 with artificial regulatory part M1-46, to obtain Dxs37-idi46, 4) replacing regulatory part (M1-12) of β-carotene synthesis gene cluster in Dxs37-idi46 with artificial regulatory part M1-93, to obtain CAR001.

Above recombinant strain 1-3 is to improve the enzymatic activity of α-ketoglutarate dehydrogenase in *E. coli* mutant B; the improvement of the enzymatic activity of α-ketoglutarate dehydrogenase in *E. coli* mutant BETA is achieved particularly by replacing original regulatory part of α-ketoglutarate dehydrogenase gene sucAB in *E. coli* mutant B with artificial regulatory part M1-46; particularly by way of homologous recombination;

Above *E. coli* mutant B (LYC001) is constructed by a method comprising step of: deleting the β-carotene cyclase gene crtX and the lycopene β-cyclase gene crtY from the carotene synthesis gene cluster of recombinant strain 1-2, to obtain *E. coli* mutant B; particularly by way of homologous recombination; (see Example 11, the construction of LYC001).

The β-carotene synthesis gene cluster is a gene cluster consisting of geranyl-geranyl diphosphate synthase gene crtE, β-carotene cyclase gene crtX, lycopene β-cyclase gene crtY, phytoene desaturase gene crtI and phytoene synthase gene crtB.

The trc regulatory part of the β-carotene synthesis gene cluster has a nucleotide sequence of SEQ ID NO: 6 in the sequence listing;

The artificial regulatory part M1-12 has a nucleotide sequence of SEQ ID NO: 7 in the sequence listing;

The original regulatory part of 1-deoxy-D-xylulose-5-phosphate synthase gene has a nucleotide sequence of SEQ ID NO: 8 in the sequence listing;

The artificial regulatory part M1-37 has a nucleotide sequence of SEQ ID NO: 10 in the sequence listing;

The original regulatory part of isopentenyl diphosphate isomerase gene idi has a nucleotide sequence of SEQ ID NO: 12 in the sequence listing;

The artificial regulatory part M1-46 has a nucleotide sequence of SEQ ID NO: 14 in the sequence listing;

The artificial regulatory part M1-93 has a nucleotide sequence of SEQ ID NO: 11 in the sequence listing;

In above recombinant strain 1, β-carotene synthesis gene cluster is inserted into *E. coli* at D-lactate dehydrogenase (ldhA) site of chromosome, which is achieved particularly by way of homologous recombination; see Example 1, II.1 for detailed method; the *E. coli* is particularly ATCC 8739.

Another object of the present invention is to provide a recombinant strain 1-1-A or a recombinant strain 1-1-B.

The present invention provides a recombinant strain 1-1-A that is constructed by a method comprising step of: introducing a β-carotene synthesis gene cluster into above recombinant strain 1-1, to obtain recombinant strain 1-1-A; the introduction of β-carotene synthesis gene cluster to above recombinant strain 1-1 is to introduce a recombinant vector, pTrc99A-M-crt (constructed by a method as seen in Example 1, 1, 2), into above recombinant strain 1-1; the recombinant vector, pTrc99A-M-crt is particularly a recombinant vector containing the β-carotene synthesis gene cluster.

The present invention provides a recombinant strain 1-1-B that is constructed by a method comprising step of: introducing a lycopene synthesis gene cluster into above recombinant strain 1-1, to obtain recombinant strain 1-1-B; the introduction of lycopene synthesis gene cluster into above recombinant strain 1-1 is to introduce a recombinant vector, pTrc99A-M-crtEIB (constructed by a method as seen in Example 11, part 1), to above recombinant strain 1-1; the recombinant vector, pTrc99A-M-crtEIB, is particularly a recombinant vector containing the lycopene synthesis gene cluster.

The lycopene synthesis gene cluster is a gene cluster consisting of geranyl-geranyl diphosphate synthase gene crtE, phytoene desaturase gene crtI and phytoene synthase gene crtB.

A third object of the present invention is to provide a recombinant strain 2.

The present invention provides a recombinant strain 2 (CAR001) that is constructed by a method comprising steps of (see Example 2 for details):
1) introducing a β-carotene synthesis gene cluster and a trc regulatory part into *E. coli*, to obtain recombinant *E. coli* (QL002);
2) replacing the trc regulatory part of β-carotene synthesis gene cluster, original regulatory part of 1-deoxy-D-xylulose-5-phosphate synthase gene dxs and original regulatory part of isopentenyl diphosphate isomerase gene idi in the recombinant *E. coli* as below, to obtain *E. coli* mutant (CAR001):

replacing the trc regulatory part of β-carotene synthesis gene cluster with artificial regulatory part M1-93;
replacing original regulatory part of 1-deoxy-D-xylulose-5-phosphate synthase gene dxs with artificial regulatory part M1-37;
replacing original regulatory part of isopentenyl diphosphate isomerase gene idi with artificial regulatory part M1-46;
above replacements of trc regulatory part of β-carotene synthesis gene cluster, original regulatory part of 1-deoxy-D-xylulose-5-phosphate synthase gene dxs and original regulatory part of isopentenyl diphosphate isomerase gene idi in recombinant *E. coli* are performed in following order of steps as below, identical to that of *E. coli* mutant A (CAR001) as described above.

The β-carotene synthesis gene cluster is a gene cluster consisting of geranyl-geranyl diphosphate synthase gene crtE, β-carotene cyclase gene crtX, lycopene β-cyclase gene crtY, phytoene desaturase gene crtI and phytoene synthase gene crtB;

The trc regulatory part of β-carotene synthesis gene cluster has a nucleotide sequence of SEQ ID NO: 6 in the sequence listing;

The artificial regulatory part M1-12 has a nucleotide sequence of SEQ ID NO: 7 in the sequence listing;

The original regulatory part of 1-deoxy-D-xylulose-5-phosphate synthase gene dxs has a nucleotide sequence of SEQ ID NO: 8 in the sequence listing;

The artificial regulatory part M1-37 has a nucleotide sequence of SEQ ID NO: 10 in the sequence listing;

The original regulatory part of isopentenyl diphosphate isomerase gene idi has a nucleotide sequence of SEQ ID NO: 12 in the sequence listing;

The artificial regulatory part M1-46 has a nucleotide sequence of SEQ ID NO: 14 in the sequence listing;

The artificial regulatory part M1-93 has a nucleotide sequence of SEQ ID NO: 11 in the sequence listing.

In above recombinant strain 2, the introduction of β-carotene synthesis gene cluster into *E. coli* is to introduce β-carotene synthesis gene cluster into *E. coli* at ldhA site of chromosome; particularly achieved by way of homologous recombination; see Example 1, II. 1 for detailed method; the *E. coli* is particularly ATCC 8739.

A fourth object of the present invention is to provide a recombinant strain 3.

The present invention provides a recombinant strain 3 that is constructed by a method comprising step of: replacing original regulatory part of α-ketoglutarate dehydrogenase gene sucAB, original regulatory part of succinate dehydrogenase gene (sdhABCD) and/or original regulatory part of transaldolase gene (Transaldolase B, talB) of above recombinant strain 2 with artificial regulatory part M1-46, to obtain recombinant strain 3;

The original regulatory part of α-ketoglutarate dehydrogenase gene sucAB has a nucleotide sequence of SEQ ID NO: 15 in the sequence listing;

The original regulatory part of succinate dehydrogenase gene sdhABCD has a nucleotide sequence of SEQ ID NO: 16 in the sequence listing;

The original regulatory part of transaldolase gene talB has a nucleotide sequence of SEQ ID NO: 17 in the sequence listing;

The artificial regulatory part M1-46 has a nucleotide sequence of SEQ ID NO: 14 in the sequence listing.

Above recombinant strain 3 is recombinant strain 3-1, 3-2, 3-3 or 3-4.

The recombinant strain 3-1 (CAR005) is constructed by a method comprising step of: replacing each of the original regulatory parts of the α-ketoglutarate dehydrogenase gene sucAB, the succinate dehydrogenase gene sdhABCD and the transaldolase gene talB in recombinant strain 2 (CAR001) with artificial regulatory part M1-46, to obtain recombinant strain 3-1; particularly by way of homologous recombination; see the method of Example 9, part 1 for details.

The recombinant strain 3-2 (CAR002/SucAB46) is constructed by a method comprising step: replacing original regulatory part of α-ketoglutarate dehydrogenase gene sucAB in recombinant strain 2 with artificial regulatory part M1-46, to obtain recombinant strain 3-2; particularly by way of homologous recombination (see Example 8, part 1 for details).

The recombinant strain 3-3 (CAR004/SucAB46-sdhABCD46) is constructed by a method comprising step of: replacing each of original regulatory part of α-ketoglutarate dehydrogenase gene sucAB and original regulatory part of succinate dehydrogenase gene sdhABCD of above recombinant strain 2 (CAR001) with artificial regulatory part M1-46, to obtain recombinant strain 3-3; particularly by way of homologous recombination (see Example 8, part 1 for details).

The recombinant strain 3-4 (CAR003) is constructed by a method comprising step of: replacing each of original regulatory part of α-ketoglutarate dehydrogenase gene sucAB and original regulatory part of transaldolase gene talB of above recombinant strain 2 (CAR001) with artificial regulatory part M1-46, to obtain recombinant strain 3-4; particularly by way of homologous recombination (see Example 9, part 1 for details).

A fifth object of the present invention is to provide a recombinant strain 4 or a recombinant strain 5.

The present invention provides a recombinant strain 4 (LYC001) that is constructed by a method comprising step of: deleting β-carotene cyclase gene crtX and lycopene β-cyclase gene crtY from the β-carotene synthesis gene cluster of above recombinant strain 2 (CAR001) to obtain recombinant strain; particularly achieved by way of homologous recombination (see Example 11, part 1 for detailed method).

The present invention provides a recombinant strain 5 that is constructed by a method comprising step of: replacing original regulatory parts of α-ketoglutarate dehydrogenase gene sucAB, transaldolase gene talB and/or succinate dehydrogenase gene sdhABCD of above recombinant strain 4 (LYC001) with artificial regulatory part M1-46;

The original regulatory part of α-ketoglutarate dehydrogenase gene sucAB has a nucleotide sequence of in the sequence listing SEQ ID NO: 15;

The original regulatory part of transaldolase gene talB has a nucleotide sequence of SEQ ID NO:17 in the sequence listing;

The original regulatory part of succinate dehydrogenase gene sdhABCD has a nucleotide sequence of SEQ ID NO: 16 in the sequence listing;

The artificial regulatory part M1-46 has a nucleotide sequence of SEQ ID NO: 14 in the sequence listing.

The recombinant strain 5 is recombinant strain 5-1, recombinant strain 5-2, or recombinant strain 5-3.

Above recombinant strain 5-1 is constructed by a method comprising step of:

replacing original regulatory part of α-ketoglutarate dehydrogenase gene sucAB of above recombinant strain 4 (LYC001) with artificial regulatory part M1-46, to obtain recombinant strain 5-1 (LYC002); by way of homologous recombination; see Example 12, part 1 for details.

Above recombinant strain 5-2 is constructed by a method comprising step of: replacing each of original regulatory parts of α-ketoglutarate dehydrogenase gene sucAB and transaldolase gene talB of above recombinant strain 4 (LYC001) with artificial regulatory part M1-46, to obtain recombinant strain 5-2 (LYC003); by way of homologous recombination; see Example 13, part 1 for details.

Above recombinant strain 5-3 is constructed by a method comprising step of: replacing each of original regulatory parts of α-ketoglutarate dehydrogenase gene sucAB, succinate dehydrogenase gene sdhABCD and transaldolase gene talB of above recombinant strain 4 (LYC001) with artificial regulatory part M1-46, to obtain recombinant strain 5-3 (LYC005); by way of homologous recombination; see Example 14, part 1 for details.

Use of above recombinant strain 1 in the production of lycopene and/or β-carotene is also within the protection scope of the present invention; or Use of above recombinant strain 1-3 in the production of lycopene is also within the protection scope of the present invention; or Use of above recombinant strain 1-1-A in the production of β-carotene is also within the protection scope of the present invention; or Use of above recombinant strain 1-1-B in the production of lycopene is also within the protection scope of the present invention; or Use of recombinant strain 2 or recombinant strain 3 in the production of β-carotene is also within the protection scope of the present invention; or Use of recombinant strain 4 or recombinant strain 5 in the production of lycopene is also within the protection scope of the present invention.

DETAILED DESCRIPTION OF CERTAIN EMBODIMENTS OF THE INVENTION

Figure 1:
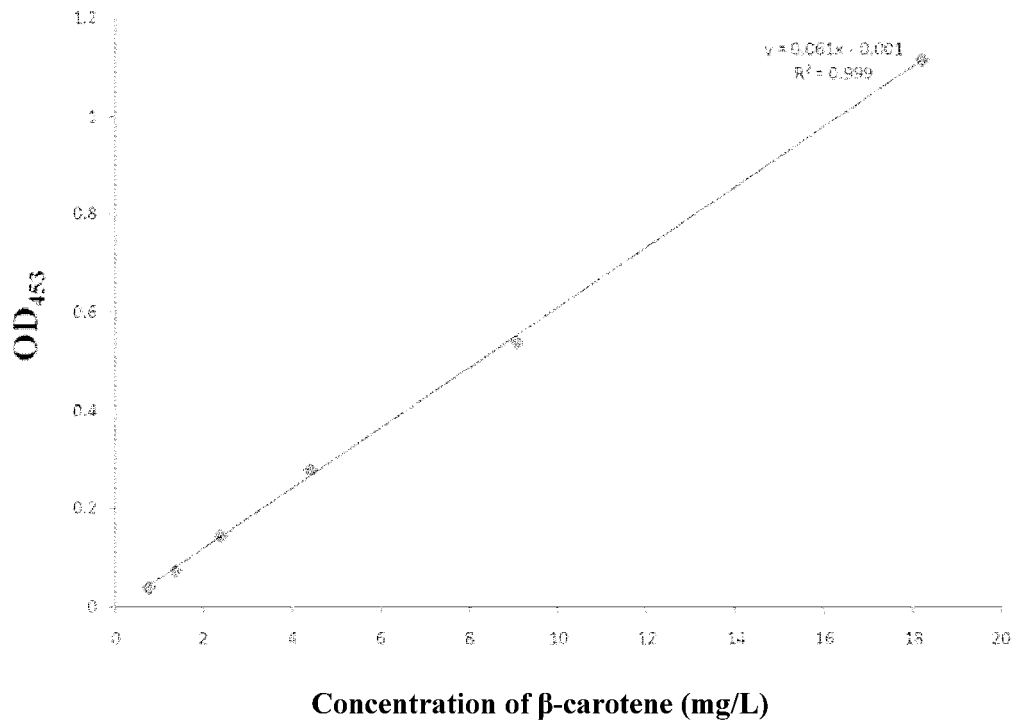
FIG. 1 is a standard curve of $OD_{453\,nm}$ vs. concentration of β-carotene.

The experimental methods employed in following Examples are conventional methods, unless otherwise specified.

All the materials, agents, etc. used in following Examples are publicly available, unless otherwise specified.

EXAMPLE 1

Introduction of β-Carotene Synthesis Gene into *E. coli* to Obtain Recombinant *E. coli*

I. Introduction of β-Carotene Synthesis Gene Via a Plasmid to Construct Recombinant *E. coli* ATCC 8739 (pACYC184-M-Crt)

IPP, DMAPP and FPP may be synthesized by *E. coli* itself via MEP pathway and FPP synthase. However, *E. coli* cannot synthesize β-carotene by itself. A cluster of β-carotene synthesis gene exists in *Pantoea agglowerans* under the same operon. The β-carotene synthesis gene cluster consists of geranyl-geranyl diphosphate (GGPP) synthase gene (crtE, SEQ ID NO: 1), β-carotene cyclase gene (crtX, SEQ ID NO: 2), lycopene β-cyclase gene (crtY, SEQ ID NO: 3), phytoene desaturase gene (crtI, SEQ ID NO: 4), and phytoene synthase gene (crtB, SEQ ID NO: 5).

1. Construction of Recombinant *E. coli* ATCC 8739 (pACYC184-M-Crt)

The β-carotene synthesis gene cluster was introduced into *E. coli* ATCC 8739 (Gunsalus I C, Hand D B. The use of bacteria in the chemical determination of total vitamin C. *J Biol Chem.* 1941, 141:853-858; publicly available from Tianjin Institute of Industrial Biotechnology), to obtain recombinant strain ATCC 8739 (pACYC184-M-crt), specifically as below:

1) PCR Amplification of DNA Fragment crtEXYIB Containing β-Carotene Synthesis Gene Cluster The sequences of the primers were:

```
crt-cluster-f:
CTGTGAATTCAAGGAGATATACCATGATGACGGTCTGTGCAGAA;

crt-cluster-r:
TTGCAGTCGACGCTGCGAGAACGTCA;
```

Underlined portions of above primers were EcoRI and SalI digestion sites, respectively, and AGGAGATATACCA was artificial RBS.

PCR amplification was performed with crt-cluster-f and crt-cluster-r as primers, and the genome of *Pantoea agglomerans* (CGMCC NO.: 1.2244, publicly available from China General Microbiological Culture Collection Center) as a template, to obtain an about 5800 bp PCR product, i.e., the DNA fragment of crtEXYIB. The PCR product comprises genes crtE, crtX, crtY, crtI and crtB.

2) Construction of Recombinant Vector pACYC184-M-Crt

A. Construction of Intermediate Vectors pTrc99A-M and pACYC 184-M

An about 1700 bp DNA fragment 1 was amplified with DNA of plasmid pTrc99A (Amann, E., Ochs, B. and Abel, K. J. Tightly regulated tac promoter vectors useful for the expression of unfused and fused proteins in *Escherichia coli*. Gene. 1988, 69:301-15. publicly available from Tianjin Institute of Industrial Biotechnology) as a template, through primer of 99A-F1-PacI-SpeI-NdeI/99A-R1-PacI, so that Pac I, Spe I and Nde I digestion sites were located before lad gene of plasmid pTrc99A, Pac I digestion site located after terminator rrnB. Fragment 1 was further digested with Dpn I, and phosphorylated with T4 polynucleotide kinase. An about 2000 bp DNA fragment 2 was amplified with DNA of plasmid pTrc99A as a template, through a primer 99A-F2/99A-R2, digested by Dpn I, and linked to phosphorylated DNA fragment 1 with quick-ligase, and then transformed into *E. coli* trans10 competent cells. The cells were cultured in LB agar plate containing a final concentration of 50 μg/mL of ampicillin overnight. 5 clones were picked, with their plasmid DNA extracted and verified using Pac I, BamH I digestions. The right positive clone was designated as pTrc99A-M.

An about 2100 bp DNA fragment 3 was amplified by the same method, with DNA of plasmid pACYC184 (Mok, Y. K., Clark, D. R., Kam, K. M. and Shaw, P. C. BsiY I, a novel thermophilic restriction endonuclease that recognizes 5' CCNNNNNNNGG 3' and the discovery of a wrongly sequenced site in pACYC177. Nucleic Acids Res. 1991, 19:2321-2323; publicly available from Tianjin Institute of Industrial Biotechnology) as a template, through a primer 184-F2/184-R2, digested by Dpn I, and linked to phosphorylated DNA fragment 1 with quick-ligase, followed by verification using Pac I, BamH I digestions. The right positive clone was designated as pACYC184-M.

The sequences of the primers were:

```
99A-F1-PacI-SpeI-NdeI:
TTAATTAACTAGTCATATGGGCATGCATTTACGTTGACA

99A-R1-PadI: TTAATTAAAGAAACGCAAAAAGGCCATC

99A-F2: CATTCAAATATGTATCCGCTCA

99A-R2: CGCAGGAAAGAACATGTGAG

184-F2: GGGAGAGCCTGAGCAAACT

184-R2: CGATGATAAGCTGTCAAACATGA.
```

B. Construction of intermediate vector pTrc99A-M-Crt: the 5800 bp DNA fragment crtEXYIB obtained in 1) was inserted into plasmid pTrc99A-M between EcoRI and SalI digestion sites, to obtain intermediate vector pTrc99A-M-crt;

Specific method was as follows: DNA fragment crtEXYIB was digested with EcoRI and SalI, and linked to similarly digested pTrc99A-M plasmid backbone (3716 bp), to obtain a recombinant vector; the recombinant vector was sent for sequencing, and the result showed that the recombinant vector was a vector wherein genes crtE, crtX, crtY, crtI and crtB were inserted into pTrc99A-M between EcoRI and SalI, which was designated as pTrc99A-M-crt.

C. Construction of recombinant vector pACYC184-M-crt: DNA fragment crtEXYIB was inserted into pACYC184-M plasmid at PacI digestion site, to obtain recombinant vector pACYC184-M-crt;

Details are as follows, the intermediate vector pTrc99A-M-crt obtained in B was digested by PacI, and an about 7.8 kb fragment was recovered by gel extraction; the recovered fragment was linked to similarly digested pACYC184-M vector that was obtained from A, to obtain a recombinant vector; the recombinant vector was sent for sequencing, and the result showed that DNA fragment crtEXYIB was inserted into pACYC184-M at PacI digestion site, and was designated as pACYC184-M-crt.

3) Construction of Recombinant *E. coli* ATCC 8739 (pACYC184-M-Crt)

The pACYC184-M-crt obtained from C was electro-transformed into *E. coli* ATCC 8739, to obtain recombinant *E. coli* ATCC 8739 (pACYC184-M-crt).

Specifically, 50 μl of *E. coli* ATCC 8739 electro-transformed competent cell was placed on ice, added with 1 μl of plasmid pACYC184-M-crt (about 50 ng/ul), and left on ice for 2 minutes, and then transferred to 0.2 cm Bio-Rad cuvette, and subjected to electric shock on a MicroPulser (Bio-Rad) electroporation apparatus, with an electric shock parameter of a voltage of 2.5 kv. Immediately after the shock, 1 ml of the LB culture medium was transferred to the cuvette, and lashed 5 times, after which it was transferred to a tube, and incubated at 75 rpm, 30° C. for 2 hours. 50 μl of the strain solution was coated on a LB plate containing chloromycetin, and incubated at 37° C. overnight, after which 5 positive single colonies were picked, and subjected to a liquid cultivation, and then plasmids of the positive single colonies were extracted for PacI digestion, to obtain a 7.8 kb positive plasmid. The recombinant strain containing the positive plasmid was designated as ATCC 8739 (pACYC184-M-crt).

2. Production of β-Carotene by Recombinant *E. coli* ATCC 8739 (pACYC184-M-Crt)

A single colony of recombinant *E. coli* ATCC 8739 (pACYC184-M-crt) was picked in a tube containing 4 ml LB (containing a final concentration of 34 μg/ml of chloromycetin), cultivated at 30° C., 250 rpm overnight; then, an amount of 1% (volume percent) of the strain solution, i.e. 100 μl of strain solution, from the tube was inoculated in 10 ml culture medium (containing corresponding antibiotics) in 100 ml Tri Flask, and cultivated at 30° C., 250 rpm; when $OD_{600}$=0.1, i.e., after about 3 h, a final concentration of 1 mM of IPTG was added for induction; with cultivation for additional 24 h, the color of the strain solution became yellow from white.

2 ml of the strain solution was subjected to centrifugation at 14000 rpm for 3 min, with supernatant being discarded, the strain cells were washed with sterilized water, and added with 1 ml acetone for extraction in dark at 55° C. for 15 min. After centrifugation at 14000 rpm for 10 min, supernatant was collected, and measured at 453 nm on an ultraviolet spectrophotometer for β-carotene absorption value thereof. The measured value was compared with corresponding cell turbidness ($OD_{600}$ nm), to obtain a relative production of β-carotene.

The supernatant was measured using HPLC (high performance liquid chromatograph 1260 Infinity, Agilent Technologies) for the content of β-carotene.

Standard β-carotene was purchased from Sigma, US (Cat. No. C4582), and a standard curve was determined immediately when the standard was received. A 0.45 μm millipore filter (Millpor) was used for filtration; acetone, methanol, dichloromethane, petroleum ether, and acetonitrile were chromatographic pure agents, supplied by Merk.

5 mg of β-carotene standard was precisely weighted, dissolved in 1 ml of dichloromethane, and diluted to 10 ml with acetone, to obtain a 500 μg/ml standard solution. When used, it was serially diluted with acetone (2×, 4×, 8×, 16×, 32×), and filtered into HPLC vials, to perform HPLC detection. Symmetry C18 column (4.6×250 mm, 5 μm); column temperature: 30° C.; mobile phase: methanol:acetonitrile:dichloromethane=21:21:8; loading volume: 20 μl; loading time: 20 min; DAD light detection; and detection wavelength of 450 nm, were employed, and the standard curve of β-carotene was obtained via the relation between peak area of the standard and the concentration of β-carotene.

Immediately after extraction from the supernatant, the content of β-carotene was measured with HPLC; the supernatant appeared yellow, and the strain became white from yellow after extraction with acetone. With a test with HPLC, the sample has an appearance time of β-carotene identical to that of the standard (an appearance time of 17.2 min).

The result, as shown in FIG. 1, showed that $OD_{453}$ nm exhibited excellent linear correlation with β-carotene concentration. After cultivation of 24 hours, ATCC 8739 (pACYC184-M-crt) was obtained with a dry cell weight of 1.55 g/L, a β-carotene yield of 0.87 mg/L, and a β-carotene amount of 0.56 mg/g dry cell weight.

Accordingly, the introduction of a set of crt genes associated with catalytic production of β-carotene in *Pantoea agglomerans* into *E. coli* in a form of plasmid, enabled *E. coli* having the function of producing β-carotene.

II. Integration of β-Carotene Synthesis Gene into *E. coli* ATCC 8739 Chromosome by Homologous Recombination to Construct Recombinant *E. coli* QL002

1. Construction of Recombinant *E. coli* QL002 by Homologous Recombination

Recombinant *E. coli* QL002 was such that β-carotene synthesis gene cluster crtEXYIB (a gene cluster consisting of geranyl-geranyl diphosphate synthase gene crtE, β-carotene cyclase gene crtX, lycopene β-cyclase gene crtY, phytoene desaturase gene crtI and phytoene synthase gene crtB) was integrated into *E. coli* ATCC 8739 chromosome at ldhA site by homologous recombination.

The method may be in reference to Jantama et al., 2008; Zhang et al., 2007, and is detailed as below:

In step 1, lactate dehydrogenase gene (ldhA) of *E. coli* ATCC 8739 was amplified with *E. coli* ATCC 8739 genomic DNA as a template and primers ldhA-up/ldhA-down.

The primers had sequences of:

```
ldhA-up:   GATAACGGAGATCGGGAATG ldhA-down: CTTTGGCTGTCAGTTCACCA.
```

The obtained 1750 bp amplification product is lactate dehydrogenase gene ldhA.

The PCR amplification product was cloned to a clone vector, pEASY-Blunt, to obtain a recombinant vector, which was then sent for sequencing. The result showed a vector pEASY-Blunt with inserted lactate dehydrogenase gene ldhA, demonstrating that the construction of the plasmid was true. The obtained recombinant plasmid was designated as pXZ001.

In step 2, PCR amplification was performed with pXZ001 plasmid DNA as a template and primers of ldhA-1/ldhA-2. The primers have sequences as follows:

```
ldhA-1: TCTGGAAAAAGGCGAAACCT ldhA-2: TTTGTGCTATAAACGGCGAGT
```

An about 4778 bp PCR amplification product was obtained, as comprising about 400 bases of upstream and downstream sequence of lactate dehydrogenase gene and the sequence of pEASY-Blunt vector.

In step 3, PCR amplification was performed with pLOI4162 plasmid (Jantama K, Zhang X, Moore J C, Shanmugam K T, Svoronos S A, Ingram L O. Eliminating side products and increasing succinate yields in engineered strains of *Escherichia coli* C. *Biotechnol Bioeng.* 2008, 101 (5): 881-893, publicly available from Tianjin Institute of Industrial Biotechnology) as a template and primers 4162-F/4162-R, to obtain a 3000 bp DNA fragment comprising a chloromycetin resistent gene (Cam) and a levansucrose transferase gene (Levansucrase, sacB).

The primers had sequences of:

```
4162-F: GGAGAAAATACCGCATCAGG

4162-R: GCGTTGGCCGATTCATTA.
```

The 4778 bp PCR amplification product obtained in step 2 was cleaned with a PCR cleaning kit, and then treated with DpnI; the about 3000 bp PCR amplification product obtained in step 3 was cleaned with a PCR cleaning kit, and then was phosphorylated; and the two fragments were linked to obtain a linked product, which was transformed into trans T1, to obtain a solution of transformed strain. 200 μl of the solution of the transformed strain was coated onto a LB plate containing kanamycin and chloromycetin, and cultivated overnight; thereafter, 5 positive single colonies were picked, and the positive clones were subjected to a liquid cultivation. Then, a positive cloned plasmid was subjected to verification by digestion, proved of that chloromycetin gene and levansucrose transferase gene had been inserted in pEASY-Blunt vector and within 400 bp homologous arms upstream and downstream of the gene encoding lactate dehydrogenase gene, and was designated as pXZ002.

In step 4, PCR amplification was performed with pXZ002 plasmid DNA as a template and primers ldhA-up/ldhA-down, to obtain an about 3700 bp DNA fragment I, which comprises about 400 bases of the upstream of gene encoding lactate dehydrogenase, Cat-sacB DNA fragment, and about 400 bases of the downstream of the lactate dehydrogenase encoding gene. The DNA fragment I was used in a first homologous recombination: pKD46 plasmid (Datsenko, wanner. One-step inactivation of chromosomal genes in *Escherichia coli* K-12 using PCR products. *Proc Natl Acad Sci USA.* 2000. 97 (12): 6640-6645; publicly available from Tianjin Institute of Industrial Biotechnology) is first transformed into *E. coli* ATCC 8739 by calcium chloride transformation, and then DNA fragment I was electro-transformed into the *E. coli* ATCC 8739 with pKD46. Immediately after an electric shock, 1 ml of the LB culture medium was transferred to a cuvette, lashed 5 times, and transferred to a tube, followed by incubation at 75 rpm, 30° C. for 2 hours. pKD46 plasmid was removed. 200 μl of the strain solution was coated on a LB agar plate containing chloromycetin, and cultivated overnight, after which 5 single colonies were picked for PCR verification (using primers ldhA-up/ldhA-down, wherein correctly amplified colony product is an about 3700 bp fragment). A right single colony was picked, and designated as QL001.

In step 5, pTrc99A-M-crt plasmid was digested with PacI, and the fragment about 8 kb was recovered by gel extraction and the ends were repaired and made blunt with Klenow Fragment, then linked to the 4778 bp PCR amplification product obtained in step 2. The ligation were transformed into trans T1 and 200 μl of the solution of transformed strain was spreaded on a LB plate containing kanamycin, and cultivated overnight, after which 5 positive single colonies were picked, and the positive clones were subjected to a liquid cultivation. A positive cloned plasmid was extracted for digestion (with PacI, to obtain a fragment of about 8 kb, as a positive plasmid) and sequenced for verification. The results showed that rtEXYIB gene was inserted in pEASY-Blunt vector and within 400 bp homologous arms of upstream and downstream of the gene encoding lactate dehydrogenase gene. It was designated as pXZ003-crt.

In step 6, an about 9000 bp DNA fragment II (comprising about 400 bases of upstream of gene encoding lactate dehydrogenase, a trc promoter, a crtEXYIB gene, a rrnB T2 transcription terminator and about 400 bases of downstream of gene encoding lactate dehydrogenase) was amplified with the DNA of pXZ003-crt plasmid as a template and primers ldhA-up/ldhA-down. DNA fragment II was used for a second homologous recombination: pKD46 plasmid was first transformed into QL001 by calcium chloride transformation, and DNA fragment II was then electrotransformed into QL001 with pKD46 plasmid, wherein the electrotransformation was conducted in the conditions that: first, electrotransformation competent cells of QL001 with pKD46 plasmid were prepared; 50 μl of competent cells was placed on ice, added with 50 ng DNA fragment II, and left on ice for 2 minutes, and then transferred to a 0.2 cm Bio-Rad cuvette. An electric shock was conducted using a MicroPulser (Bio-Rad) electroporation apparatus, with an electric shock parameter of a voltage of 2.5 kv. Thereafter, 1 ml of the LB culture medium was immediately transferred to the cuvette, lashed 5 times, and then transferred to a tube, followed by incubation at 75 rpm, 30° C. for 4 hours. pKD46 plasmid was removed. The strain solution was transferred to a LB liquid culture medium (a 250 ml Tri Flask charged with 50 ml culture medium) containing 10% sucrose, free of sodium chloride, and cultivated for 24 hours, and then subjected to a streak culture in a LB solid culture medium containing 6% sucrose, free of sodium chloride. With a PCR verification (using primers ldhA-up/crtE-r, the right colony amplification product is an about 4500 bp fragment), a right single colony was picked, and designated as QL002.

The crtE-r primer has a sequence of:

```
crtE-r: TTAACTGACGGCAGCGAGTT.
```

2. Production of β-Carotene by Recombinant *E. coli* QL002

A single colony of recombinant *E. coli* QL002 was picked and placed into 4 ml of a tube with a LB culture medium, and cultivated at 30° C., 250 rpm overnight; then, an amount of 1% (volume percent) of the strain solution, i.e. 100 μl of strain solution, in the tube was inoculated in 10 ml of a culture medium in a 100 ml Tri Flask, and cultivated at 30° C., 250 rpm; when $OD_{600}=0.1$, i.e., after about 3 h, a final concentration of 1 mM of IPTG was added for induction; after additional 24 h, samples were taken to determine the yield of β-carotene.

By a method for the determination as seen in above experiment I, as a result, QL002 had a β-carotene yield up to 0.59 mg/L, β-carotene content up to 0.41 mg/g dry cell weight.

EXAMPLE 2

Construction of Recombinant E. coli CAR001 and Fermentation

The construction of recombinant E. coli CAR001 and fermentation thereby were divided into following 8 steps:
1 Improvement of the Expression Strength of the β-Carotene Synthesis Gene Cluster of Recombinant E. coli QL002 and Construction of Recombinant E. coli QL105

Recombinant E. coli QL105 was such that the trc regulatory part (SEQ ID NO: 6 in the sequence listing) of the β-carotene synthesis gene cluster crtEXYIB of QL002 was replaced with an artificial regulatory part M1-12 (SEQ ID NO: 7 in the sequence listing) by a two-step homologous recombination.

With the two-step homologous recombination, the artificial regulatory part was inserted before the gene to be regulated, and no resistant gene or FRT marker was left after the operation. In a first step homologous recombination, original regulatory part of the gene was replaced with a cat-sacB fragment; and in a second step homologous recombination, the cat-sacB fragment was replaced with artificial regulatory parts with various strengths. The fragments used in the two-step homologous recombination were amplified by a PCR method with two pairs of general primers. Using gene-cat-up (including 50 bp bases before artificial regulatory part inserting site and a 20 bp homologous fragment of cat-sacB gene) and gene-cat-down (including 50 bp bases after artificial regulatory part inserting site and another homologous fragment of cat-sacB gene), DNA fragment I was amplified, to perform the first step homologous recombination. Using gene-up-P (including 50 bp bases before artificial regulatory part inserting site and a 20 bp homologous fragment of the artificial regulatory part) and gene-RBS-down (including 50 bp bases after artificial regulatory part inserting site and another homologous fragment of the artificial regulatory part) primers, DNA fragment II was amplified, to perform the second step homologous recombination.

It is detailed specifically as below.
In step 1, the starting vector was pXZ002 plasmid, amplification primers were ldhA-cat-up/crtE-cat-down, the strain to be transformed was recombinant E. coli QL002, and identification primers were ldhA-up/crtE-340-down; specifically as below:

PCR amplification was performed with amplification primers ldhA-cat-up/crtE-cat-down and the starting vector pXZ002 plasmid as a template, to obtain an about 3800 bp DNA fragment I (ldhA-catsacB-crtE), which fragment comprised about 50 bases upstream of ldhA gene, DNA fragment Cat-sacB, about 50 bases upstream of crtE.

ldhA-cat-up:
ATTAAATTTGAAATTTTGTAAAATATTTTTAGTAGCTTAAATGTGATTC

ATGTGACGGAAGATCACTTCGCA

-continued
crtE-cat-down:
GCATCGCTGTGTATGAAATTGACGTGTTGTTCTGCACAGACCGTCATC

ATTTATTTGTTAACTGTTAATTGTCCTTG

The PCR amplification product of DNA fragment I obtained in step 1 was cleaned with a PCR cleaning kit, treated with DpnI, and then used for a first homologous recombination: the pKD46 plasmid was first transformed into recombinant E. coli QL002 by calcium chloride transformation, and then DNA fragment I was electrotransformed into the E. coli QL002 with pKD46. After electric shock, 1 ml of LB culture medium was immediately transferred to the cuvette, and lashed 5 times, and then it was transferred to a tube, and incubated at 75 rpm, 30° C. for 2 hours. 200 μl of the strain solution was coated onto a LB plate containing chloromycetinaminobenzyl, and after an overnight culture, screened on a LB plate containing chloromycetinaminobenzyl and a kanamycin containing LB plate, respectively, to obtain a clone that is not grown with kanamycin, but grown on the chloromycetinaminobenzyl LB plate, which was verified by PCR (using identification primers of ldhA-up/crtE-340-down, whereby a right colony amplification product was an about 4000 bp fragment), to obtain an intermediate positive clone, for a second step homologous recombination.

crtE-340-down: GCGACATGTTCACCATACTG

In step 2, the starting strain was a recombinant strain M1-12, the amplification primers were ldhA-up-p and crtE-RBS-down, the strain to be transformed was an intermediate positive clone, and the identification primers were the same as above (ldhA-up/crtE-340-down); specifically as below:

PCR amplification was performed with amplification primers ldhA-up-p and crtE-RBS-down, and genomic DNA of recombinant strain M1-12 (Lu J, Tang J L, Liu Y, Zhu X, Zhang T, Zhang X. Combinatorial modulation of galP and glk gene expression for improved alternative glucose utilization. *Appl Microbiol Biotechnol.* 2012, 93:2455-2462; publicly available from Tianjin Institute of Industrial Biotechnology) as a template, and an about 200 bp DNA fragment II was obtained, which contained about 50 bases downstream of ldhA gene, artificial regulatory part fragment M1-12, and about 50 bases upstream of crtE.

ldhA-up-P:
ATTAAATTTGAAATTTTGTAAAATATTTTTAGTAGCTTAAATGTGATTC

ATTATCTCTGGCGGTGTTGAC crtE-RBS-down:
GCATCGCTGTGTATGAAATTGACGTGTTGTTCTGCACAGACCGTCATC

ATAGCTGTTTCCTGGTT

DNA fragment II was electrotransformed into the intermediate positive clone obtained from step 1. After electric shock, 1 ml of LB culture medium was immediately transferred to the cuvette, and lashed 5 times, and then it was transferred to a tube, and cultivated at 75 rpm, 30° C. for 4 hours, after which it was transferred to 50 ml of LB+10% sucrose medium free of salt in flask. After 24 h, it was streaked on a LB+6% sucrose arga plate free of salt, and cultivated at 41° C. overnight to remove the pKD46 plasmid. The strains were screened on a LB plate containing chloromycetin and a LB plate free of antibiotic. The clones that was not grown on the LB plate containing chloromycetin were verified by PCR using identification primers ldhA-up/crtE-340-down. Right colony amplification product was an about 1000 bp fragment. The stain with right sequencing was designated as recombinant E. coli QL105.

2. Production of β-Carotene by Recombinant *E. coli* QL105

A single colony of recombinant *E. coli* QL105 was picked into 4 ml of LB culture medium in a tube, and cultivated at 30° C., 250 rpm overnight; then, an amount of 1% (volume percent) of the strain solution, i.e. 100 ul of the strain solution, in the tube was inoculated to 10 ml of a culture medium in a 100 ml Tri Flask, and cultivated at 30° C., 250 rpm for 24 h. Thereafter, samples were taken for determining β-carotene yield. The method for the determination was as seen in Example 1.

As a result, the β-carotene yield of QL105 was up to 2.17 mg/L, and the content of β-carotene was up to 1.53 mg/g dry cell weight.

3. Improvement of the Expression Strength of Recombinant *E. coli* QL105 Dxs Gene and Construction of Recombinant *E. coli* Dxs64, Dxs37, Dxs93

Recombinant *E. coli* Dxs64, Dxs37, Dxs93 were prepared, respectively, in a way as the two-step homologous recombination in Example 2, part 1, wherein original regulatory part (SEQ ID NO: 8) of recombinant *E. coli* QL105 dxs gene was replaced with artificial regulatory part M1-64 (SEQ ID NO: 9), M1-37 (SEQ ID NO: 10), and M1-93 (SEQ ID NO: 11), respectively.

Construction of Recombinant *E. coli* Dxs64 (Two-Step Homologous Recombination):

Step 1: the same as Step 1 of part 1 in Example 2, except that the starting vector was pLOI4162 plasmid, the amplification primers were dxs-cat-up/dxs-cat-down, an about 3400 bp DNA fragment I was obtained, and the strain to be transformed was recombinant *E. coli* QL105; an intermediate positive clone was obtained.

dxs-cat-up:
ACTACATCATCCAGCGTAATAAATAAACAATAAGTATTAATAGGCCCCT

GGGAGAAAATACCGCATCAGG dxs-cat-down:
GTGGAGTCGACCAGTGCCAGGGTCGGGTATTTGGCAATATCAAAAC TC

ATGCGTTGGCCGATTCATTA

Step 2: the same as Step 2 of part 1 in Example 2, except that the starting strain was a recombinant strain M1-64 (Lu J, Tang J L, Liu Y, Zhu X, Zhang T, Zhang X. Combinatorial modulation of galP and glk gene expression for improved alternative glucose utilization. *Appl Microbiol Biotechnol.* 2012, 93:2455-2462; publicly available from Tianjin Institute of Industrial Biotechnology), the amplification primers were dxs-up-P and dxs-RBS-down, an about 200 bp DNA fragment II was obtained, and the strain to be transformed was an intermediate positive clone got in step 1. Recombinant *E. coli* Dxs64 was obtained.

In both of above two steps, the identification primers were dxs-up-480F and dxs-down-381R (The correct PCR fragment was about 900 bp).

dxs-up-480F: AGTGGTATTGCCGGAATG dxs-down-381R: GATGGAGGTTGATGAATGC

Construction of recombinant *E. coli* Dxs37 (two-step homologous recombination): substantially the same as recombinant *E. coli* Dxs64, except that the starting strain in step 2 was a recombinant strain M1-37 (Lu J, Tang J L, Liu Y, Zhu X, Zhang T, Zhang X. Combinatorial modulation of galP and glk gene expression for improved alternative glucose utilization. *Appl Microbiol Biotechnol.* 2012, 93:2455-2462; publicly available from Tianjin Institute of Industrial Biotechnology), an about 200 bp DNA fragment II was obtained;

Preparation of recombinant *E. coli* Dxs93 (two-step homologous recombination): substantially the same as recombinant *E. coli* Dxs64, except that the starting strain in step 2 was a recombinant strain M1-93 (Lu J, Tang J L, Liu Y, Zhu X, Zhang T, Zhang X. Combinatorial modulation of galP and glk gene expression for improved alternative glucose utilization. *Appl Microbiol Biotechnol.* 2012, 93:2455-2462; publicly available from Tianjin Institute of Industrial Biotechnology), an about 200 bp DNA fragment II was obtained;

With a correct sequencing verification, the strains in which the regulatory part of dxs gene of QL105 was replaced with artificial regulatory parts M1-64, M1-37, M1-93, respectively, were designated as recombinant *E. coli* Dxs64, Dxs37, Dxs93, respectively.

4. Production of β-Carotene by Recombinant *E. coli* Dxs64, Dxs37, Dxs93

Fermentation culturing of recombinant *E. coli* QL105, Dxs64, Dxs37, Dxs93 were performed in a way the same as in Example 1, and the yields of β-carotene were determined As seen from the results shown in Table 1, with the regulation of dxs, β-carotene yield was improved by 1.8-2.3 folds; the maximum β-carotene yield was from M1-37 regulatory part, and the minimum was from M1-93 regulatory part.

TABLE 1

Improvement of β-carotene production by regulations of genes dxs, idi and crt

| Strain | OD600 | Dry weight (g/L) | OD453 | β-carotene content (mg/L) | β-carotene yield (mg/g) | Increased folds |
|---|---|---|---|---|---|---|
| QL105 | 4.39 ± 0.00 | 1.42 ± 0.00 | 0.26 ± 0.01 | 2.17 ± 0.00 | 1.53 ± 0.00 | 1.0 |
| Monogene regulation | | | | | | |
| Dxs64 | 3.72 ± 0.01 | 1.20 ± 0.01 | 0.45 ± 0.00 | 3.66 ± 0.00 | 3.05 ± 0.00 | 2.0 |
| Dxs37 | 3.76 ± 0.16 | 1.21 ± 0.16 | 0.53 ± 0.16 | 4.32 ± 0.13 | 3.56 ± 0.18 | 2.3 |
| Dxs93 | 3.93 ± 0.05 | 1.27 ± 0.05 | 0.43 ± 0.02 | 3.55 ± 0.01 | 2.80 ± 0.00 | 1.8 |
| Digene regulation | | | | | | |
| Dxs37-Idi30 | 4.64 ± 0.13 | 1.50 ± 0.13 | 0.74 ± 0.03 | 6.09 ± 0.03 | 4.07 ± 0.00 | 2.7 |
| Dxs37-Idi46 | 4.40 ± 0.00 | 1.42 ± 0.00 | 0.92 ± 0.01 | 7.58 ± 0.01 | 5.33 ± 0.01 | 3.5 |
| Dxs37-Idi37 | 4.51 ± 0.00 | 1.46 ± 0.00 | 0.77 ± 0.04 | 6.30 ± 0.04 | 4.32 ± 0.04 | 2.8 |

TABLE 1-continued

Improvement of β-carotene production by regulations of genes dxs, idi and crt

| Strain | OD600 | Dry weight (g/L) | OD453 | β-carotene content (mg/L) | β-carotene yield (mg/g) | Increased folds |
|---|---|---|---|---|---|---|
| Trigene regulation | | | | | | |
| CAR001 | 4.31 ± 0.01 | 1.39 ± 0.01 | | 25.67 ± 0.01 | 18.40 ± 0.01 | 12.0 |

5. Regulation of the Expression Strength of Recombinant *E. coli* Dxs37 Idi Gene and Construction of Recombinant *E. coli* Dxs37-Idi30, Dxs37-Idi46, Dxs37-Idi37

Recombinant *E. coli* Dxs37-Idi30, Dxs37-Idi46, and Dxs37-Idi37 were prepared, respectively, in a way as the two-step homologous recombination in Example 2, part 1, wherein original regulatory part (SEQ ID NO: 12) of idi gene of Dxs37 prepared in above part 3 was replaced with artificial regulatory part M1-30 (SEQ ID NO: 13), M1-46 (SEQ ID NO: 14), and M1-37 (SEQ ID NO: 10), respectively.

Construction of Recombinant *E. coli* Dxs37-Idi30: (Two-Step Homologous Recombination):

Step 1: as Step 1 of part 1 of Example 2, except that the starting vector was pLOI4162 plasmid, the amplification primers were idi-cat-up/idi-cat-down, an about 3400 bp DNA fragment I was obtained, and the strain to be transformed was recombinant *E. coli* Dxs37; to obtain an intermediate positive clone.

idi-cat-up:
TCACTTGGTTAATCATTTCACTCTTCAATTATCTATAATGATGAGTGAT

CTGTGACGGAAGATCACTTCGCA idi-cat-down:
CCCGTGGGAACTCCCTGTGCATTCAATAAAATGACGTGTTCCGTTTGCA

TTTATTTGTTAACTGTTAATTGTCCTTG

Step 2: as Step 2 of part 1 of Example 2, except that the starting strain was a recombinant strain M1-30 (Lu J, Tang J L, Liu Y, Zhu X, Zhang T, Zhang X. Combinatorial modulation of galP and glk gene expression for improved alternative glucose utilization. *Appl Microbiol Biotechnol.* 2012, 93:2455-2462; publicly available from Tianjin Institute of Industrial Biotechnology), the amplification primers were idi-up-p and idi-RBS-down, an about 200 bp DNA fragment II was obtained, and the strain to be transformed was the intermediate positive clone got in step 1. Recombinant *E. coli* Dxs37-Idi30 was obtained.

idi-up-p:
TCACTTGGTTAATCATTTCACTCTTCAATTATCTATAATGATGAGTGAT

CTTATCTCTGGCGGTGTTGAC idi-RBS-down:
CCCGTGGGAACTCCCTGTGCATTCAATAAAATGACGTGTTCCGTTTGCA

TAGCTGTTTCCTGGTT

In both of above two steps, the identification primers were Idi-up and idi-down (the correct PCR fragment was about 900 bp).

Idi-up: ATGACTCCGACGCTCTCTCA idi-down: CGTGGCATCAATACCGTGTA

Construction method (two-step homologous recombination) of recombinant *E. coli* Dxs37-Idi46: substantially the same as that of recombinant *E. coli* Dxs37-Idi30, except that the starting strain in Step 2 was a recombinant strain M1-46 (Lu J, Tang J L, Liu Y, Zhu X, Zhang T, Zhang X. Combinatorial modulation of galP and glk gene expression for improved alternative glucose utilization. *Appl Microbiol Biotechnol.* 2012, 93:2455-2462; publicly available from Tianjin Institute of Industrial Biotechnology), an about 200 bp DNA fragment II was obtained;

Construction method (two-step homologous recombination) of recombinant *E. coli* Dxs37-Idi37: substantially the same as that of recombinant *E. coli* Dxs37-Idi30, except that the starting strain in Step 2 was a recombinant strain M1-37, an about 200 bp DNA fragment II was obtained;

After verified as right with sequencing, the strains in which original regulatory part of idi gene of Dxs37 was replaced with artificial regulatory parts M1-30, M1-46, and M1-37, respectively, were designated as recombinant *E. coli* Dxs37-Idi30, Dxs37-Idi46, and Dxs37-Idi37, respectively.

6. Production of β-Carotene by Recombinant *E. coli* Dxs37-Idi30, Dxs37-Idi46, Dxs37-Idi37

Fermentation culturing of recombinant *E. coli* Dxs37-Idi30, Dxs37-Idi46, and Dxs37-Idi37 were performed in a way as that in Example 1, to determine β-carotene yields.

The results are seen in Table 1. With a combined regulation of dxs and idi, β-carotene yield was improved by 2.7-3.5 folds; and maximum of the β-carotene yield was from Dxs37-Idi46 strain.

7. Construction of Recombinant Strain CAR001 with Improved Expression of β-Carotene Synthesis Gene Cluster of Recombinant *E. coli* Dxs37-Idi46

Recombinant strain CAR001 was constructed from recombinant *E. coli* Dxs37-Idi46 which regulatory part M1-12 (SEQ ID NO: 7) of β-carotene synthesis gene cluster crtEXYIB replaced with artificial regulatory part M1-93 (SEQ ID NO: 11); for which a specific method is as below:

Construction of Recombinant *E. coli* CAR001 (Two-Step Homologous Recombination):

Step 1: as Step 1 of part 1 in Example 2, except that the starting vector was pXZ002 plasmid, the amplification primers were ldhA-cat-up/crtE-cat-down, an about 3800 bp DNA fragment I was obtained, and the strain to be transformed was recombinant *E. coli* Dxs37-Idi46, and the identification primers were ldhA-up/crtE-340-down, an intermediate positive clone was obtained.

ldhA-cat-up:
ATTAAATTTGAAATTTTGTAAAATATTTTTAGTAGCTTAAATGTGATTC

ATGTGACGGAAGATCACTTCGCA

-continued crtE-cat-down:
GCATCGCTGTGTATGAAATTGACGTGTTGTTCTGCACAGACCGTCATCA

TTTATTTGTTAACTGTTAATTGTCCTTG

Step 2: as Step 2 of part 1 in Example 2, except that the starting strain was M1-93, the amplification primers were amplification primers ldhA-up-p and crtE-RBS-down, an about 200 bp DNA fragment II was obtained, and the strain to be transformed was the intermediate positive clone got in step 1. Recombinant E. coli CAR001 was obtained.

ldhA-up-P:
ATTAAATTTGAAATTTTGTAAAATATTTTTAGTAGCTTAAATGTGATTC

ATTATCTCTGGCGGTGTTGAC crtE-RBS-down:
GCATCGCTGTGTATGAAATTGACGTGTTGTTCTGCACAGACCGTCATCA

TAGCTGTTTCCTGGTT

In above two steps, the identification primers were ldhA-up/crtE-340-down, and the correct amplification band was about 900 bp.

ldhA-up: GATAACGGAGATCGGGAATG crtE-340-down: GCGACATGTTCACCATACTG

8. Production of β-Carotene by Recombinant Strain CAR001

A Fermentation culturing of recombinant E. coli CAR001 was performed in a way as that in Example 1, to determine a β-carotene yield.

As can be seen from the results shown in Table 1, in comparison with recombinant E. coli QL105, the resulting strain CAR001 from the regulation of crt gene had β-carotene content increased by 12 folds. The β-carotene yield was up to 25.67 mg/L, and the β-carotene content was up to 18.4 mg/g dry cell weight.

EXAMPLE 3

Improvement of Expression Strength of α-Ketoglutarate Dehydrogenase Gene of Recombinant E. coli CAR001

1. Improvement of Expression Strength of α-Ketoglutarate Dehydrogenase Gene of Recombinant E. coli CAR001 and Construction of Recombinant Strains SucAB46-FKF, SucAB37-FKF, and SucAB93-FKF Recombinant E. coli SucAB46-FKF, SucAB37-FKF, and SucAB93-FKF were, respectively, recombinant E. coli CAR001 having original regulatory part (SEQ ID NO: 15) of α-ketoglutarate dehydrogenase gene (sucAB) replaced with artificial regulatory parts M1-46 (SEQ ID NO: 14), M1-37 (SEQ ID NO: 10), and M1-93 (SEQ ID NO: 11), respectively.

Original regulatory region of a gene on a chromosome of E. coli was replaced with artificial regulatory parts having various intensities through a pair of general primers using one-step homologous recombination. An upstream primer was gene-up-FRT, comprising 50 bases outside the original regulatory region of the gene to be regulated and 20 bases homologous with FRT sequence. A downstream primer was gene-RBS-down, comprising 15 bases homologous with the ribosome bind site of E. coli lacZ gene and 50 bases after the initiation codon of the gene to be regulated.

1800 bp DNA fragments sucAB-M1-46, sucAB-M1-37 and sucAB-M1-93 were amplified, with sucAB-up-FRT and sucAB-RBS-down as primers, and with recombinant strains M1-46, M1-37, M1-93 as templates; and after one-step homologous recombination of sucAB-M1-46 and E. coli CAR001, a recombinant E. coli SucAB46-FKF was obtained, specifically as below:

Firstly, pKD46 plasmid was transformed into E. coli CAR001 by calcium chloride transformation. Next, DNA fragment sucAB-M1-46 was electrotransformed into E. coli CAR001 with pKD46. The electrotransformation was performed in the conditions that: competent cells of E. coli CAR001 with pKD46 plasmid to be electrotransformed were firstly prepared; 50 μl of the competent cell was placed on ice, added with 50 ng of the DNA fragment, and left to stand on ice for 2 minutes, and then transferred to a 0.2 cm Bio-Rad cuvette. After electric shock was performed using an MicroPulser (Bio-Rad) electroporation apparatus, with an electric shock parameter of a voltage of 2.5 kv, 1 ml of the LB culture medium was immediately transferred to the cuvette, and lashed 5 times, and then it was transferred to a tube, and cultivated at 75 rpm, 30° C. for 2 hours. 100 μl of the strain solution was coated onto LB plates containing kanamycin, respectively, and cultivated at 41° C. overnight. pKD46 plasmid was removed. A recombinant strain SucAB46-FKF was obtained.

In the same way of one-step homologous recombination, recombinant E. coli SucAB37-FKF was obtained by homologous recombination of sucAB-M1-37 and E. coli CAR001; and recombinant E. coli SucAB93-FKF was obtained by homologous recombination of sucAB-M1-93 and E. coli CAR001;

Above recombinant E. coli strains were identified by PCR using kan-f and sucAB-r, and the correct PCR fragment was about 900 bp The primers had sequences of:

sucAB-up-FRT:
CAGTGTATGTCCGAAGGGGCTGAACCCGACGCGCGCCATCGGCCATATCA

GTGTAGGCTGGAGCTGCTTC sucAB-RBS-down:
CCAGAGAGGTAAGAAGAGTCCAACCAGGCTTTCAAAGCGCTGTTCTGCAT

AGCTGTTTCCTGGTT.

The primers for PCR verification had sequences of:

kan-f: CCGTGATATTGCTGAAGAG sucAB-r: GAAATATTCACGCGTTTGAG.

After verifying the right clones by sequencing, the strains, in which original regulatory part of sucAB gene of CAR001 was respectively replaced with artificial regulatory part M1-46, M1-37, and M1-93, were designated as recombinant E. coli SucAB46-FKF, SucAB37-FKF, and SucAB93-FKF, respectively.

2. Production of β-Carotene

Fermentation culturing of recombinant E. coli SucAB46-FKF (M1-46), SucAB37-FKF (M1-37), and SucAB93-FKF (M1-93) were performed in a way as that of Example 1, to determine β-carotene yields.

Figure 2:
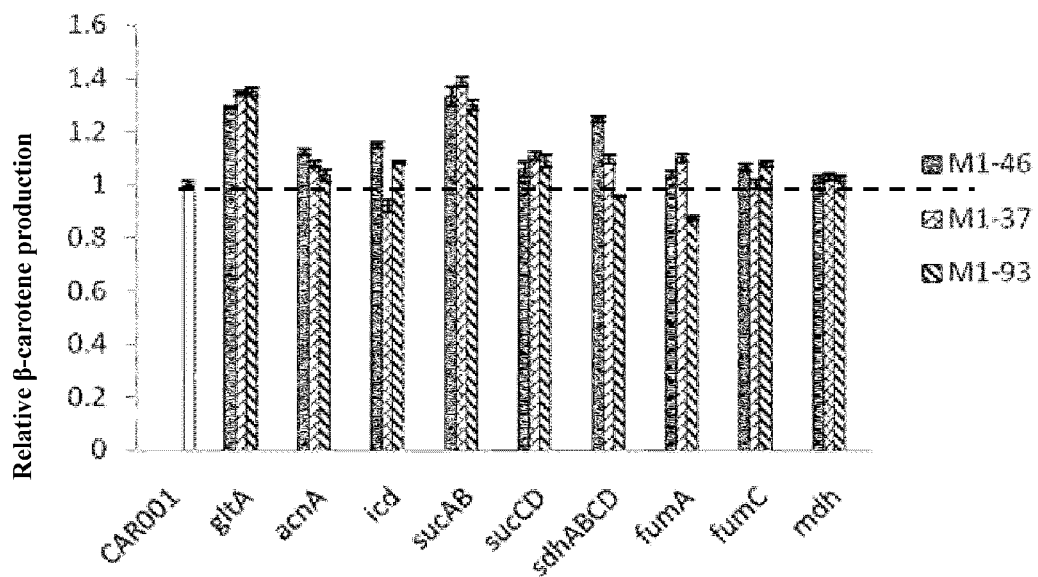
FIG. 2 shows change in β-carotene production after regulation of key genes of TCA pathway, citrate synthase gene (gltA), aconitase gene (acnA), icd, sucAB, sucCD, sdhABCD, fumarase A (fumA), fumarase C (fumC), and mdh gene, in recombinant E. coli CAR001.

The results are seen in FIG. 2. The β-carotene yields of recombinant *E. coli* SucAB46-FKF (M1-46), SucAB37-FKF (M1-37), and SucAB93-FKF (M1-93) were 24.47 mg/g, 25.58 mg/g, and 23.92 mg/g, respectively; after the regulation of sucAB, as compared with CAR001, M1-37 had the maximum improvement of β-carotene yield of 39%.

EXAMPLE 4

Improvement of Expression Strength of Succinate Dehydrogenase Gene of Recombinant *E. coli* CAR001

1 Improvement of the Expression Strength of Succinate Dehydrogenase Gene of Recombinant *E. coli* CAR001 and Construction of the Recombinant Strain Recombinant *E. coli* Sdh46-FKF, Sdh37-FKF, and Sdh93-FKF were recombinant *E. coli* CAR001 having original regulatory part (SEQ ID NO: 16) of succinate dehydrogenase gene (sdhABCD) replaced with artificial regulatory part M1-46 (SEQ ID NO: 14), M1-37 (SEQ ID NO: 10), and M1-93 (SEQ ID NO: 11), respectively.

1800 bp DNA fragments sdhABCD-M1-46, sdhABCD-M1-37 and sdhABCD-M1-93 were amplified by the one-step homologous recombination method of Example 3, part 1, with sdhABCD-up-FRT and sdhABCD-RBS-down as primers, and recombinant strains M1-46, M1-37, M1-93 as a template, respectively; after a homologous recombination of sdhABCD-M1-46 and *E. coli* CAR001, recombinant *E. coli* Sdh46-FKF was obtained; after a homologous recombination of sdhABCD-M1-37 and *E. coli* CAR001, recombinant *E. coli* Sdh37-FKF was obtained; and after a homologous recombination of sdhABCD-M1-46 and *E. coli* CAR001, recombinant *E. coli* Sdh46-FKF was obtained; these were identified by PCR using kan-f and sdhABCD-r, and the correct PCR fragment was about 900 bp.

```
sdhABCD-up-FRT:
ACTTTGTTGAATGATTGTCAAATTAGATGATTAAAAATTAAATAAATGTT

GTGTAGGCTGGAGCTGCTTC sdhABCD-RBS-down:
TTAACAGGTCTTTGTTTTTTCACATTTCTTATCATGAATAACGCCCACAT

AGCTGTTTCCTGGTT
```

The primers for the PCR verification had sequences of:

```
kan-f:  CCGTGATATTGCTGAAGAG sdhABCD-r:  AATTTGACGAAGAAGCTGC.
```

After verifying the right clones by sequencing, the strains, in which original regulatory part of sdhABCD gene of CAR001 was respectively replaced with artificial regulatory parts M1-46, M1-37, and M1-93, were designated as recombinant *E. coli* Sdh46-FKF, Sdh37-FKF, and Sdh93-FKF, respectively.

2. Production of β-Carotene by Recombinant *E. coli* Sdh46-FKF, Sdh37-FKF, and Sdh93-FKF Fermentation culturing of recombinant *E. coli* Sdh46-FKF (M1-46), Sdh37-FKF (M1-37), and Sdh93-FKF (M1-93) were performed in a way as that of Example 1, to determine β-carotene yields.

The results are show in FIG. 2. The β-carotene yields of recombinant *E. coli* Sdh46-FKF (M1-46), Sdh37-FKF (M1-37), and Sdh93-FKF (M1-93) were 23 mg/g, 20.06 mg/g, and 17.48 mg/g, respectively; after the regulation of sdhABCD, as compared with CAR001, M1-46 had the maximum improvement of β-carotene yield of 25%.

EXAMPLE 5

Improvement of Expression Strength of Transaldolase Gene of Recombinant *E. coli* CAR001

1 Improvement of the Expression Strength of Transaldolase Gene (talB) of Recombinant *E. coli* CAR001 and Construction of Recombinant Strains talB46, talB37, and talB93

Recombinant strains talB46, talB37, and talB93 were recombinant *E. coli* CAR001 having original regulatory part (SEQ ID NO: 17) of transaldolase gene (talB) replaced with artificial regulatory parts M1-46 (SEQ ID NO: 14), M1-37 (SEQ ID NO: 10), and M1-93 (SEQ ID NO: 11), respectively.

Construction of Recombinant Strain talB46 (Two-Step Homologous Recombination):

Step 1: as Step 1 of part 1 in Example 2, except that the starting vector was pLOI4162 plasmid, the amplification primers were talB-cat-up and talB-cat-down, an about 3400 bp DNA fragment I was obtained, and the strain to be transformed was recombinant *E. coli* CAR001; an intermediate positive clone was obtained.

Step 2: as Step 2 of part 1 in Example 2, except that the starting strain was M1-46, the amplification primers were talB-up-P and talB-RBS-down, an about 200 bp DNA fragment II was obtained, and the strain to be transformed was the intermediate positive clone got in step 1. Recombinant *E. coli* talB46 was obtained.

The primers for the amplification in Step 1 had sequences of:

```
talB-cat-up:
AGTCTCGCCTGGCGATAACCGTCTTGTCGGCGGTTGCGCTGACGTTGCG

TCGTGTGTGACGGAAGATCACTTCGCA talB-cat-down:
TCATGATAGTATTTCTCTTTAAACAGCTTGTTAGGGGGATGTAACCGGTC

TGCTTATTTGTTAACTGTTAATTGTCCT
```

The primers talB-up-P/talB-RBS-down for the amplification in Step 2 had sequences of:

```
talB-up-P:
AGTCTCGCCTGGCGATAACCGTCTTGTCGGCGGTTGCGCTGACGTTGCG

TCGTGTTATCTCTGGCGGTGTTGAC talB-RBS-down:
AGTGTCGGCCACTACGGTGGTGTACTGACGAAGGGAGGTCAATTTGTCC

GTCATAGCTGTTTCCTGGTT
```

In above two steps, the identification primers were talB-up/talB-down with sequences of (the correct PCR fragment was about 900 bp):

```
talB-up:  CGGATGTAGCGAAACTGCAC talB-down:  GACGCTTCGGTGTCATAGGAAAG.
```

Construction of recombinant *E. coli* talB 37: in a way substantially the same as that for recombinant *E. coli* talB46, except that the starting strain in Step 2 was replaced with M1-37, an about 200 bp DNA fragment II was obtained;

Construction of recombinant E. coli talB 93: in a way substantially the same as that for recombinant E. coli talB46, except that the starting strain in Step 2 was replaced with M1-93, to obtain an about 200 bp DNA fragment II;

After verifying the right clones by sequencing, the strains, in which original regulatory part of talB gene of CAR001 was respectively replaced with artificial regulatory parts M1-46, M1-37, and M1-93, were designated as recombinant E. coli talB46, talB37, and talB93, respectively.

2. Production of β-Carotene by Recombinant E. coli talB46, talB37, talB93

Fermentation culturing of recombinant E. coli talB46 (M1-46), talB37 (M1-37), and talB93 (M1-93) were performed in a way as Example 1, to determine β-carotene yields.

Figure 3:
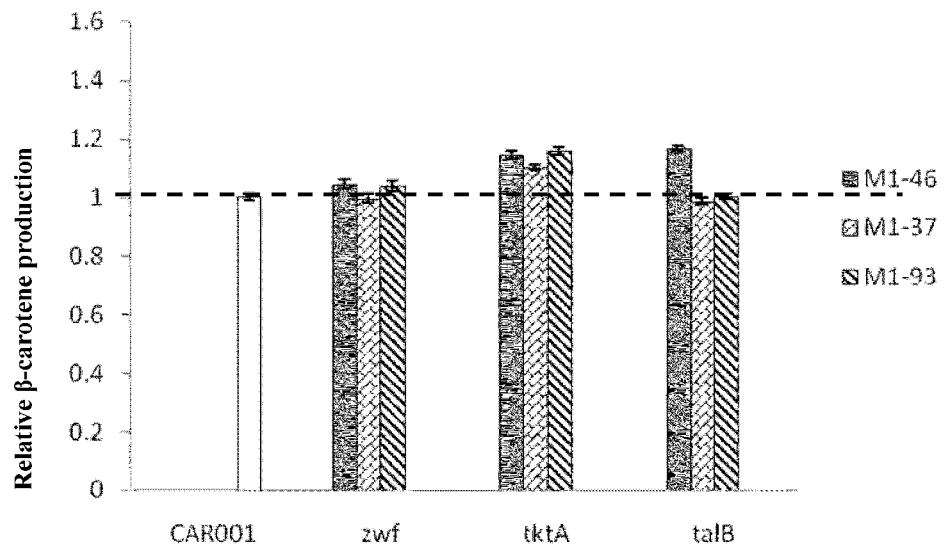
FIG. 3 shows change in β-carotene production after regulation of key genes of pentose phosphate pathway, transketolase (transketolase I, tktA), talB, and glucose 6-phosphate-1-dehydrogenase (zwf) gene, in recombinant *E. coli* CAR001.

The results were shown in FIG. 3. The β-carotene yields of recombinant E. coli talB46 (M1-46), talB37 (M1-37), and talB93 (M1-93) were 21.53 mg/g, 18.22 mg/g, and 18.58 mg/g, respectively; after the regulation of talB, as compared with CAR001, M1-46 had the maximum improvement of β-carotene yield of 17%.

EXAMPLE 6

Improvement of Expression Strength of Citrate Synthase Gene, Aconitase Gene, Isocitrate Dehydrogenase Gene, Succinyl-CoA Synthetase Gene, Fumarase Gene and Malate Dehydrogenase Gene of Recombinant E. coli CAR001

1. Improvement of the Expression Strength of Citrate Synthase Gene of Recombinant E. coli CAR001

As the one-step homologous recombination method in Example 3, part 1, original regulatory part (SEQ ID NO: 18) of citrate synthase gene (gltA) of recombinant E. coli CAR001 was replaced with artificial regulatory parts M1-46 (SEQ ID NO: 14), M1-37 (SEQ ID NO: 10), and M1-93 (SEQ ID NO: 11), to obtain recombinant GltA46-FKF, GltA37-FKF, and GltA93-FKF, respectively.

Specifically as below: 1800 bp DNA fragments gltA-M1-46, gltA-M1-37 and gltA-M1-93 were amplified with glta-up-FRT and glta-RBS-down as primers, and recombinant strains M1-46, M1-37, M1-93 as a template, respectively; after homologous recombination of gltA-M1-46 and E. coli CAR001, recombinant E. coli gltA 46-FKF was obtained; after homologous recombination of gltA-M1-37 and E. coli CAR001, recombinant E. coli gltA 37-FKF was obtained; and after homologous recombination of gltA-M1-46 and E. coli CAR001, recombinant E. coli gltA 46-FKF was obtained; these were identified by PCR with kan-f and gltA-r, and the correct PCR fragment was about 900 bp.

The primers used were:

```
glta-up-FRT:
TGTTCCGGAGACCTGGCGGCAGTATAGGCCGTTCACAAAATCATTACAA

TGTGTAGGCTGGAGCTGCTTC glta-RBS-down:
TCAACAGCTGTGTCCCCGTTGAGGGTGAGTTTTGCTTTTGTATCAGCCAT

AGCTGTTTCCTGGTT.
```

The primers for the PCR verification had sequences of:

```
kan-f: CCGTGATATTGCTGAAGAG gltA-r: TCCAGGTAGTTAGAATCGGTC
```

Fermentation culturing of recombinant E. coli GltA46-FKF, GltA37-FKF, and GltA93-FKF were performed in a way of Example 1, to determine β-carotene yields.

The results are show in FIG. 2. After the regulation of gltA, the β-carotene yields of recombinant E. coli GltA46-FKF, GltA37-FKF, and GltA93-FKF were 23.74 mg/g, 24.66 mg/g, and 24.84 mg/g, respectively; as compared with CAR001, M1-93 had the maximum improvement of β-carotene yield of 35%.

2 Improvement of the Expression Strength of Aconitase Gene (Aconitate Hydratase) of Recombinant E. coli CAR001

As the process of one-step homologous recombination in Example 3, part 1, original regulatory part (SEQ ID NO: 19) of aconitase gene (acnA) of recombinant E. coli CAR001 was replaced with artificial regulatory parts M1-46 (SEQ ID NO: 14), M1-37 (SEQ ID NO: 10), and M1-93 (SEQ ID NO: 11), respectively, to obtain AcnA46-FKF, AcnA37-FKF, and AcnA93-FKF.

Specifically as below: 1800 bp DNA fragments acnA-M1-46, acnA-M1-37 and acnA-M1-93 were amplified with acnA-up-FRT and acnA-RBS-down as primers, and recombinant strains M1-46, M1-37, M1-93 as a template, respectively; after homologous recombination of acnA-M1-46 and E. coli CAR001, recombinant E. coli acnA 46-FKF was obtained; after homologous recombination of acnA-M1-37 and E. coli CAR001, recombinant E. coli acnA 37-FKF was obtained; and after homologous recombination of acnA-M1-46 and E. coli CAR001, recombinant E. coli acnA 46-FKF was obtained; these were identified by PCR with kan-f and acnA-r, and the correct PCR fragment was about 900 bp.

The primers used were:

```
acnA-up-FRT:
TAGAACTGTTTGCTGAAGATGATCAGCCGAAACAATAATTATCATCATTC

GTGTAGGCTGGAGCTGCTTC acnA-RBS-down:
TCTTTGGCCTGCAACGTGTCCTTACTGGCTTCTCGTAGGGTTGACGACAT

AGCTGTTTCCTGGTT.
```

The primers for the PCR verification had sequences of:

```
kan-f: CCGTGATATTGCTGAAGAG acnA-r: GTAAAGTCCTGCATCAGCAC.
```

Fermentation culturing of recombinant E. coli AcnA46-FKF, AcnA37-FKF, and AcnA93-FKF were performed in a way of Example 1, to determine β-carotene yields.

The results are show in FIG. 2. The β-carotene yields of recombinant E. coli AcnA46-FKF, AcnA37-FKF, and AcnA93-FKF were 20.61 mg/g, 19.87 mg/g, and 18.95 mg/g, respectively; after the regulation of acnA, as compared with CAR001, M1-46 had the maximum improvement of β-carotene yield of 12%.

3 Improvement of the Expression Strength of Isocitrate Dehydrogenase Gene of Recombinant E. coli CAR001

In the way of Example 3, part 1, original regulatory part (SEQ ID NO: 20) of isocitrate dehydrogenase gene (icd) of recombinant E. coli CAR001 was replaced with artificial regulatory parts M1-46 (SEQ ID NO: 14), M1-37 (SEQ ID NO: 10), and M1-93 (SEQ ID NO: 11), respectively, to obtain Icd46-FKF, Icd37-FKF, and Icd93-FKF.

Specifically as below: 1800 bp DNA fragments icd-M1-46, icd-M1-37 and icd-M1-93 were amplified with icd-up-FRT and icd-RBS-down as primers, and recombinant strains M1-46, M1-37, M1-93 as a template, respectively; after homologous recombination of icd-M1-46 and E. coli CAR001, recombinant E. coli icd 46-FKF was obtained; after homologous recombination of icd-M1-37 and E. coli CAR001, recombinant E. coli icd 37-FKF was obtained; and after homologous recombination of icd-M1-46 and E. coli CAR001, recombinant E. coli icd 46-FKF was obtained; these were identified by PCR with kan-f and icd-r, and the correct PCR fragment was about 900 bp.

The primers used were:

```
icd-up-FRT:
ATAGCCTAATAACGCGCATCTTTCATGACGGCAAACAATAGGGTAGTATT
GTGTAGGCTGGAGCTGCTTC icd-RBS-down:
TGCAGGGTGACTTCTTGCCTTGTGCCGGAACAACTACTTTACTTTCCATA
GCTGTTTCCTGGTT.
```

The primers for the PCR verification had sequences of:

```
kan-f: CCGTGATATTGCTGAAGAG icd-r: ACCGGTGTAAATTTCCATCC.
```

Fermentation culturing of recombinant E. coli Icd46-FKF, Icd37-FKF, and Icd93-FKF were performed in the way of Example 1, to determine β-carotene yields.

The results are show in FIG. 2. The β-carotene yields of recombinant E. coli Icd46-FKF (M1-46), Icd37-FKF (M1-37), and Icd93-FKF (M1-93) were 21.16 mg/g, 16.93 mg/g, and 19.87 mg/g, respectively; after the regulation of icd, as compared with CAR001, M1-46 had the maximum improvement of β-carotene yield of 15%.

4 Improvement of the Expression Strength of Succinyl-CoA Synthetase Gene of Recombinant E. coli CAR001

As the process of the one-step homologous recombination in Example 3, part 1, original regulatory part (SEQ ID NO: 21) of succinyl-CoA synthetase gene (SucCD) of recombinant E. coli CAR001 was replaced with artificial regulatory parts M1-46 (SEQ ID NO: 14), M1-37 (SEQ ID NO: 10), and M1-93 (SEQ ID NO: 11), respectively, to obtain SucCD46-FKF, SucCD37-FKF, and SucCD93-FKF.

Specifically as below: 1800 bp DNA fragments sucC-M1-46, sucC-M1-37 and sucC-M1-93 were amplified with sucC-up-FRT and sucC-RBS-down as primers, and recombinant strains M1-46, M1-37, and M1-93 as a template, respectively; after homologous recombination of sucC-M1-46 and E. coli CAR001, recombinant E. coli sucC 46-FKF was obtained; after homologous recombination of sucC-M1-37 and E. coli CAR001, recombinant E. coli sucC 37-FKF was obtained; and after homologous recombination of sucC-M1-46 and E. coli CAR001, recombinant E. coli sucC 46-FKF was obtained; these were identified by PCR with kan-f and sucC-r, and the correct PCR fragment was about 900 bp.

The primers used were:

```
sucC-up-FRT:a
TTCGGTCTACGGTTTAAAAGATAACGATTACTGAAGGATGGACAGAACAC
GTGTAGGCTGGAGCTGCTTC sucC-RBS-down:
AAGCCATAGCGGGCAAAAAGTTGTTTTGCCTGATATTCATGTAAGTTCAT
AGCTGTTTCCTGGTT.
```

The primers for the PCR verification had sequences of:

```
kan-f: CCGTGATATTGCTGAAGAG sucC-r: TGATACGTTACCAGACGCTT.
```

Fermentation culturing of recombinant E. coli SucCD46-FKF, SucCD37-FKF, and SucCD93-FKF were performed in the way of Example 1, to determine β-carotene yields.

The results are show in FIG. 2. The β-carotene yields of recombinant E. coli SucCD46-FKF (M1-46), SucCD37-FKF (M1-37), and SucCD93-FKF (M1-93) were 19.32 mg/g, 20.42 mg/g, and 20.06 mg/g, respectively; after the regulation of sucCD, as compared with CAR001, M1-37 had the maximum improvement of β-carotene yield of 11%.

5. Improvement of the Expression Strength of Fumarase Gene of Recombinant E. coli CAR001

As the process of the one-step homologous recombination in Example 3, part 1, original regulatory part (SEQ ID NO: 22) of fumarase A gene (Fumarase A, fumA) and original regulatory part (SEQ ID NO: 23) of fumarase C gene (Fumarase C, fumC) of recombinant E. coli CAR001 were replaced with artificial regulatory parts M1-46 (SEQ ID NO: 14), M1-37 (SEQ ID NO: 10), and M1-93 (SEQ ID NO: 11), respectively, to obtain FumA46-FKF, FumA37-FKF, FumA93-FKF, FumC46-FKF, FumC37-FKF, and FumC93-FKF.

Specifically as below: 1800 bp DNA fragments fumA-M1-46, fumA-M1-37 and fumA-M1-93 were amplified with fumA-up-FRT and fumA-RBS-down as primers, and recombinant strains M1-46, M1-37, M1-93 as a template, respectively; after homologous recombination of fumA-M1-46 and E. coli CAR001, recombinant E. coli fumA 46-FKF was obtained; after homologous recombination of fumA-M1-37 and E. coli CAR001, recombinant E. coli fumA 37-FKF was obtained; and after homologous recombination of fumA-M1-46 and E. coli CAR001, recombinant E. coli fumA 46-FKF was obtained; these were identified by PCR with kan-f and fumA-r, and the correct PCR fragment was about 900 bp.

1800 bp DNA fragments fumC-M1-46, fumC-M1-37 and fumC-M1-93 were amplified with fumC-up-FRT and fumC-RBS-down as primers, and recombinant strains M1-46, M1-37, M1-93 as a template, respectively; after homologous recombination of fumC-M1-46 and E. coli CAR001, recombinant E. coli fumC46-FKF was obtained; after homologous recombination of fumC-M1-37 and E. coli CAR001, recombinant E. coli fumC37-FKF was obtained; and after homologous recombination of fumC-M1-46 and E. coli CAR001, recombinant E. coli fumC46-FKF was obtained; these were identified by PCR with kan-f and fumC-r, and the correct PCR fragment was about 900 bp.

The primers used were:

```
fumA-up-FRT:
GGAGCCGCAAAAAGTCGTACTAGTCTCAGTTTTTGTTAAAAAAGTGTGTA

GTGTAGGCTGGAGCTGCTTC fumA-RBS-down:
TCTTTTTTGAGTGGAAAAGGAGCCTGATAATGAAAGGGTTTGTTTGAC

ATAGCTGTTTCCTGGTT fumC-up-FRT:
CTCACACAGTGCACTCGCTGTGTGAAATAAACAGAGCCGCCCTTCGGGGC

GTGTAGGCTGGAGCTGCTTC fumC-RBS-down:
GGGACATCAATCGCCCCCATCGAATCTTTTTCGCTGCGTACTGTATTCA

TAGCTGTTTCCTGGTT.
```

The primers for the PCR verification had sequences of:

```
kan-f:  CCGTGATATTGCTGAAGAG fumA-r: CGAGTAGCGCAAATTATCTT fumC-r: ATTCGTCGTCATGCTGTC.
```

Fermentation culturing of recombinant E. coli FumA46-FKF, FumA37-FKF, FumA93-FKF, FumC46-FKF, FumC37-FKF, and FumC93-FKF were performed in the way of Example 1, to determine β-carotene yields.

The results are show in FIG. 2. The β-carotene yields of recombinant E. coli FumA46-FKF (M1-46), FumA37-FKF (M1-37), FumA93-FKF (M1-93), FumC46-FKF (M1-46), FumC37-FKF (M1-37), and FumC93-FKF (M1-93) were 18.95 mg/g, 20.24 mg/g, 16.01 mg/g, 19.50 mg/g, 18.4 mg/g, and 19.87 mg/g, respectively; after the regulation of fumA, as compared with CAR001, M1-37 had the maximum improvement of β-carotene yield of 10%; after the regulation of fumC, as compared with CAR001, M1-93 had the maximum improvement of β-carotene yield of 8%.

6. Improvement of the Expression Strength of Malate Dehydrogenase Gene of Recombinant E. coli CAR001

As the process of the one-step homologous recombination in Example 3, part 1, original regulatory part (SEQ ID NO: 24) of malate dehydrogenase gene (mdh) of recombinant E. coli CAR001 was replaced with artificial regulatory parts M1-46 (SEQ ID NO: 14), M1-37 (SEQ ID NO: 10), and M1-93 (SEQ ID NO: 11), respectively, to obtain Mdh46-FKF, Mdh37-FKF, and Mdh93-FKF.

Specifically as below: 1800 bp DNA fragments mdh-M1-46, mdh-M1-37 and mdh-M1-93 were amplified with mdh-up-FRT and mdh-RBS-down as primers, and recombinant strains M1-46, M1-37, M1-93 as a template, respectively; after homologous recombination of mdh-M1-46 and E. coli CAR001, recombinant E. coli mdh 46-FKF was obtained; after homologous recombination of mdh-M1-37 and E. coli CAR001, recombinant E. coli mdh 37-FKF was obtained; and after homologous recombination of mdh-M1-46 and E. coli CAR001, recombinant E. coli mdh 46-FKF was obtained; these were identified by PCR with kan-f and mdh-r, and the correct PCR fragment was about 900 bp.

The primers used were:

```
mdh-up-FRT:
AGAAACATGCCTGCGTCACGGCATGCAAATTCTGCTTAAAAGTAAATT

GTGTAGGCTGGAGCTGCTTC mdh-RBS-down:
GCAAGCGCCTGGCCAATACCGCCAGCAGCGCCGAGGACTGCGACTTTCAT

AGCTGTTTCCTGGTT.
```

The primers for the PCR verification had sequences of:

```
kan-f:  CCGTGATATTGCTGAAGAG mdh-r:  CCTGAAGAAGGCTGAAATA.
```

Fermentation culturing of recombinant E. coli Mdh46-FKF, Mdh37-FKF, and Mdh93-FKF were performed in the way of Example 1, to determine β-carotene yields.

The results are show in FIG. 2. The β-carotene yields of recombinant E. coli Mdh46-FKF (M1-46), Mdh37-FKF (M1-37), and Mdh93-FKF (M1-93) were 18.77 mg/g, 18.95 mg/g, 18.77 mg/g, respectively; after the regulation of mdh, as compared with CAR001, M1-37 had the maximum improvement of β-carotene yield of 3%.

EXAMPLE 7

Improvement of Expression Intensities of 6-Phosphate-Glucose 1-Dehydrogenase Gene and Transketolase Gene of Recombinant E. coli CAR001

1 Improvement of the Expression Strength of 6-Phosphate-Glucose 1-Dehydrogenase Gene of Recombinant E. coli CAR001

In the way similar to that in Example 5, original regulatory part (SEQ ID NO: 25) of 6-phosphate-glucose 1-dehydrogenase gene (zwf) of recombinant E. coli CAR001 was replaced with artificial regulatory parts M1-46 (SEQ ID NO: 14), M1-37 (SEQ ID NO: 10), and M1-93 (SEQ ID NO: 11), respectively, to obtain recombinant E. coli zwf46, zwf37, and zwf93.

Construction of Recombinant E. coli Zwf46 (Two-Step Homologous Recombination):

Step 1: as Step 1 of part 1 in Example 2, except that the starting vector was pXZ002 plasmid, the amplification primers were zwf-cat-up and zwf-cat-down, an about 3400 bp DNA fragment I was obtained, and the strain to be transformed was recombinant E. coli CAR001; an intermediate positive clone was obtained.

Step 2: as Step 2 of part 1 in Example 2, except that the starting strain was M1-46, the amplification primers were zwf-up-P and zwf-RBS-down, an about 200 bp DNA fragment II was obtained, and the strain to be transformed was the intermediate positive clone got in step 1. Recombinant E. coli zwf46 was obtained.

Construction of recombinant E. coli zwf37: in a way substantially the same as that of recombinant E. coli zwf46, except that the starting strain in Step 2 was replaced with M1-37, an about 200 bp DNA fragment II was obtained;

Construction of recombinant E. coli zwf93: in a way substantially the same as that of recombinant E. coli zwf46, except that the starting strain in Step 2 was replaced with M1-93, to obtain an about 200 bp DNA fragment II;

The primers used were:

```
zwf-cat-up:
ATCAGTTTTGCCGCACTTTGCGCGCTTTTCCCGTAATCGCACGGGTGGA

TAAGTGTGACGGAAGATCACTTCGCA zwf-cat-down:
CCAGGGTATACTTGTAATTTTCTTACGGTGCACTGTACTGCTTTTACGA

GCTTGTTATTTGTTAACTGTTAATTGTCCT zwf-up-P:
ATCAGTTTTGCCGCACTTTGCGCGCTTTTCCCGTAATCGCACGGGTGGA

TAAGTTATCTCTGGCGGTGTTGAC zwf-RBS-down:
GCGCCGAAAATGACCAGGTCACAGGCCTGGGCTGTTTGCGTTACCGC

CATAGCTGTT TCCTGGTT.
```

In above two steps, the identification primers were zwf-up and zwf-down with sequences of (the correct PCR fragment was about 900 bp):

```
ApI-up: TTATCTCTGGCGGTGTTGAC zwf-down: CGGTTTAGCATTCAGTTTTGCC.
```

Fermentation culturing of recombinant E. coli zwf46, zwf37, and zwf93 were performed in the way of Example 1, to determine β-carotene yields.

The results were shown in FIG. 3. The β-carotene yields of recombinant E. coli zwf46 (M1-46), zwf37 (M1-37), and zwf93 (M1-93) were 19.32 mg/g, 18.4 mg/g, and 19.14 mg/g, respectively; after the regulation of zwf, as compared with CAR001, M1-46 had the maximum improvement of β-carotene yield of 5%.

2. Improvement of the Expression Strength of Transketolase Gene of Recombinant E. coli CAR001

In a way similar to that of Example 5, original regulatory part (SEQ ID NO: 26) of transketolase gene (tktA) of recombinant E. coli CAR001 was replaced with artificial regulatory parts M1-46 (SEQ ID NO: 14), M1-37 (SEQ ID NO: 10), and M1-93 (SEQ ID NO: 11), respectively, to obtain recombinant strains tktA46, tktA37, and tktA93.

Construction of Recombinant E. coli tktA46 (Two-Step Homologous Recombination):

Step 1: as Step 1 of part 1 in Example 2, except that the starting vector was pXZ002 plasmid, the amplification primers were tktA-cat-up and tktA-cat-down, an about 3400 bp DNA fragment I was obtained, and the strain to be transformed was recombinant E. coli CAR001; an intermediate positive clone was obtained.

Step 2: as Step 2 of part 1 in Example 2, except that the starting strain was M1-46, the amplification primers were tktA-up-P and tktA-RBS-down, an about 200 bp DNA fragment II was obtained, and the strain to be transformed was the intermediate positive clone got in step 1. Recombinant E. coli zwf46 was obtained.

In above two steps, the identification primers were tktA-up and tktA-down with sequences of (the correct PCR fragment was about 900 bp):

```
tktA-up: TCAGGAAATCACGCCACA tktA-down: ATCCGTCATCATATCCATCA.
```

Construction of recombinant E. coli tktA37: in a way substantially the same as that of recombinant E. coli tktA46, except that the starting strain in Step 2 was replaced with M1-37, an about 200 bp DNA fragment II was obtained;

Construction of recombinant E. coli tktA93: in a way substantially the same as that of recombinant E. coli tktA46, except that the starting strain in Step 2 was replaced with M1-93, to obtain an about 200 bp DNA fragment II;

The primers used were:

```
tktA-cat-up:
AAATGCGCCGTTTGCAGGTGAATCGACGCTCAGTCTCAGTATAAGGAAG

CGTTGGCCGATTCATTA tktA-cat-down:
TCCATGCTCAGCGCACGAATAGCATTGGCAAGCTCTTTACGTGAGGAC

ATGGAGAAAATACCGCATCAGG tktA-up-P:
AAATGCGCCGTTTGCAGGTGAATCGACGCTCAGTCTCAGTATAAGGAA

TTATCTCTGGCGGTGTTGAC tktA-RBS-down:
TCCATGCTCAGCGCACGAATAGCATTGGCAAGCTCTTTACGTGAGGAC

ATAGCTGTTTCCTGGTT.
```

Fermentation culturing of recombinant E. coli tktA46, tktA37, and tktA93 were performed in the way of Example 1, to determine β-carotene yields.

The results were shown in FIG. 3. The β-carotene yields of recombinant E. coli tktA46, tktA37, and tktA93 were 20.98 mg/g, 20.24 mg/g, and 21.34 mg/g, respectively; after the regulation of tktA, as compared with CAR001, M1-93 had the maximum improvement of β-carotene yield of 16%.

EXAMPLE 8

Combined Improvement of Expression Intensities of α-Ketoglutarate Dehydrogenase Gene and Succinate Dehydrogenase Gene of Recombinant E. coli CAR001

Recombinant E. coli SucAB46, and SucAB37 were from recombinant E. coli CAR001 which original regulatory part (SEQ ID NO: 15) of α-ketoglutarate dehydrogenase gene (sucAB) replaced with artificial regulatory parts M1-46 (SEQ ID NO: 14), and M1-37 (SEQ ID NO: 10), respectively.

Construction of Recombinant E. coli SucAB46 (Two-Step Homologous Recombination):

Step 1: as Step 1 of part 1 in Example 2, except that the starting vector was pLOI4162 plasmid, the amplification primers were SucAB-cat-up and SucAB-cat-down, and the strain to be transformed was recombinant E. coli CAR001; an about 3400 bp DNA fragment I, an intermediate positive clone was obtained.

Step 2: as Step 2 of part 1 in Example 2, except that the starting strain was M1-46, the amplification primers were SucAB-up-P and SucAB-RBS-down, an about 200 bp DNA fragment II was obtained, and the strain to be transformed was the intermediate positive clone got in step 1. Recombinant E. coli SucAB46 was obtained.

The primers for the amplification in Step 1 were:

```
SucAB-cat-up:
GGTAGTATCCACGGCGAAGTAAGCATAAAAAAGATGCTTAAGGGATCACG

TGTGACGGAAGATCACTTCGCA

SucAB-cat-down:
CCAGAGAGGTAAGAAGAGTCCAACCAGGCTTTCAAAGCGCTGTTCTGCAT

TTATTTGTTAACTGTTAATTGTCCT
```

The primers for the amplification in Step 2 were SucAB-up-P/SucAB-RBS-down with sequences of:

```
SucAB-up-P: GGTAGTATCCACGGCGAAGTAAGCATAAAA.
```

In above two steps, the identification primers were as below (an amplified fragment of about 400 bp was positive):

```
ApI-up: TTATCTCTGGCGGTGTTGAC sucAB-r: GAAATATTCACGCGTTTGAG.
```

Construction of recombinant *E. coli* SucAB 37: in a way substantially the same as that of recombinant *E. coli* SucAB46, except that the starting strain in Step 2 was M1-37, an about 200 bp DNA fragment II was obtained;

After verifying the right clones by sequencing, the strains, in which original regulatory part of sucAB gene of CAR001 was replaced with artificial regulatory parts M1-46 and M1-37, respectively, were designated as recombinant *E. coli* SucAB46 and SucAB37.

Recombinant *E. coli* sdhABCD46 and sdhABCD37 were recombinant *E. coli* CAR001 having original regulatory part (SEQ ID NO: 16) of succinate dehydrogenase gene (sdhABCD) replaced with artificial regulatory part M1-46, and M1-37, respectively.

In a similar way, the primers used for the amplification in Step 1 were:

```
SdhABCD-cat-up:
ACTTTGTTGAATGATTGTCAAATTAGATGATTAAAAATTAAATAAATGTT

TGTGACGGAAGATCACTTCGCA

SdhABCD-cat-down:
TTAACAGGTCTTTGTTTTTTCACATTTCTTATCATGAATAACGCCCACAT

TTATTTGTTAACTGTTAATTGTCCT,
``` to obtain an about 3400 bp DNA fragment I;

The primers for the amplification in Step 2 were SdhABCD-up-P/SdhABCD-RBS-down with sequences of:

```
SdhABCD-up-P:
ACTTTGTTGAATGATTGTCAAATTAGATGATTAAAAATTAAATAAATGTT

TTATCTCTGGCGGTGTTGAC

SdhABCD-RBS-down:
TTAACAGGTCTTTGTTTTTTCACATTTCTTATCATGAATAACGCCCACAT

AGCTGTTTCCTGGTT
``` to obtain an about 200 bp DNA fragment II;

The primers for the PCR verification had sequences of (an amplified fragment of about 400 bp was positive):

```
ApI-up: TTATCTCTGGCGGTGTTGAC sdhABCD-r: AATTTGACGAAGAAGCTGC.
```

After verifying the right clones by sequencing, the strains, in which original regulatory part of sdhABCD gene of CAR001 was replaced with artificial regulatory parts M1-46 and M1-37, respectively, were designated as recombinant *E. coli* sdhABCD46 and sdhABCD37.

In a similar way, the expression of sdhABCD gene of SucAB46 and SucAB37 were regulated by artificial regulatory part M1-46 and M1-37, respectively, by methods substantially the same as those of recombinant *E. coli* sdhABCD46 and sdhABCD37, except that the strain to be transformed in Step 1 was SucAB46 or SucAB37. After verifying the right clones by sequencing, the strains, in which original regulatory part of sdhABCD gene of SucAB46 and SucAB37 was replaced with artificial regulatory parts M1-46 and M1-37, respectively, were designated as recombinant *E. coli* SucAB46-sdhABCD46, SucAB46-sdhABCD37, SucAB37-sdhABCD46, and SucAB37-sdhABCD37.

2. Production of β-Carotene

Fermentation culturing of recombinants *E. coli* SucAB46, SucAB37, sdhABCD46, sdhABCD37, SucAB46-sdhABCD46, SucAB46-sdhABCD37, SucAB37-sdhABCD46, and SucAB37-sdhABCD37 were performed in the way of Example 1, to determine β-carotene yields.

Figure 4:
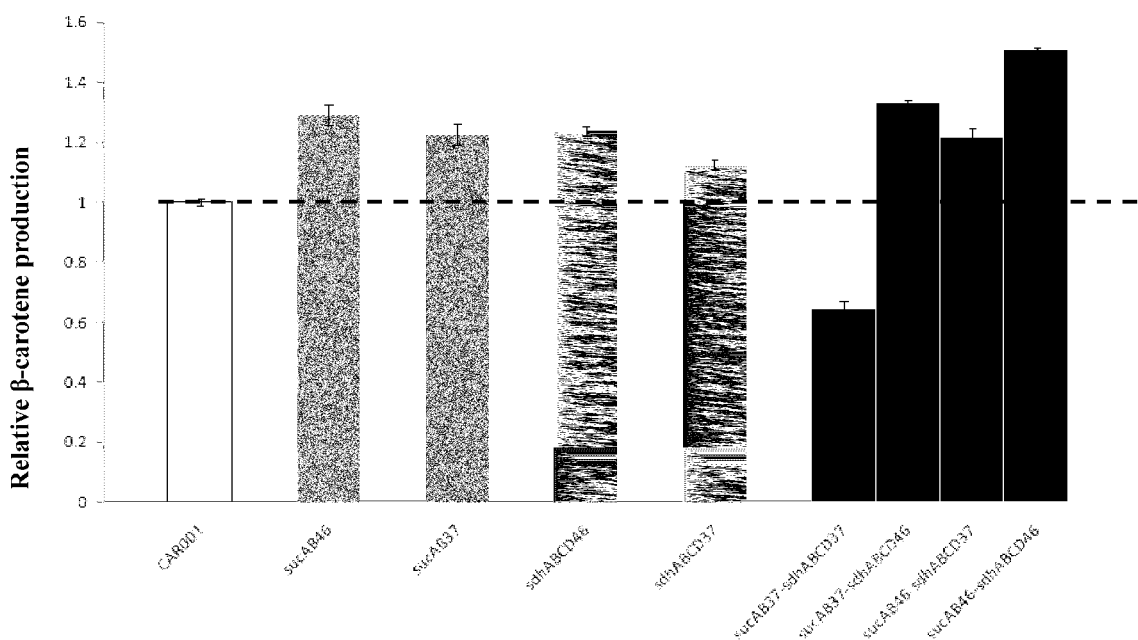
FIG. 4 shows change in β-carotene production after regulation of genes sucAB, sdhABCD and a combination thereof in recombinant *E. coli* CAR001.

The results were shown in FIG. 4. The β-carotene yields of recombinants *E. coli* SucAB46, SucAB37, sdhABCD46, sdhABCD37, SucAB46-sdhABCD46, SucAB46-sdhABCD37, SucAB37-sdhABCD46, and SucAB37-sdhABCD37 were 23.77 mg/g, 22.59 mg/g, 22.76 mg/g, 20.72 mg/g, 27.78 mg/g, 22.45 mg/g, 24.47 mg/g, and 11.96 mg/g, respectively; as can be seen, after the regulation of sucAB, as compared with CAR001, M1-46 had the maximum improvement of β-carotene yield of 29%, which was re-designated as CAR002 (SucAB46); after combined regulation of sucAB and sdhABCD, as compared with CAR001, SucAB46-sdhABCD46 had the maximum improvement of β-carotene yield of 51%, which was re-designated as CAR004.

EXAMPLE 9

Combined Modification of TCA Function Module and PPP Function Module of Recombinant *E. coli* CAR001 to Improve the Production of β-Carotene 1. Combined Modification of TCA Function Module and PPP Function Module of Recombinant *E. coli* CAR001

Recombinant *E. coli* CAR003 was recombinant *E. coli* SucAB46 (obtained from Example 8) having original regulatory part (SEQ ID NO: 17) of talB gene replaced with artificial regulatory part M1-46.

Specifically as below:

Step 1: as Step 1 of part 1 in Example 2, except that the starting vector was pLOI4162 plasmid, the amplification primers were talB-cat-up and talB-cat-down, an about 3400 bp DNA fragment I was obtained; the strain to be transformed was recombinant *E. coli* SucAB46; an intermediate positive clone was obtained.

Step 2: as Step 2 of part 1 in Example 2, except that the starting strain was M1-46, the amplification primers were talB-up-p and talB-RBS-down, an about 200 bp DNA fragment II was obtained; the strain to be transformed was the intermediate positive clone got in step 1. Recombinant E. coli CAR003 was obtained.

In the two steps, the identification primers were talB-up and talB-down (an obtained fragment of about 900 bp was positive).

After verifying the right clones by sequencing, the strains, in which original regulatory part of talB gene of SucAB46 was replaced with artificial regulatory part M1-46, were designated as recombinant E. coli CAR003, respectively.

Recombinant E. coli CAR005 was recombinant E. coli CAR004 (obtained from Example 8) having original regulatory part (SEQ ID NO: 17) of talB gene replaced with artificial regulatory part M1-46; by a method substantially the same as that of recombinant E. coli CAR003, except that the starting strain in Step 1 was replaced with CAR004.

2. Production of β-Carotene

Fermentation culturing of recombinant E. coli CAR005 was performed in the way of Example 1, to determine the β-carotene yield.

The results are seen in Table 2. As compared with CAR001, the β-carotene yield of CAR005 was improved by 64%.

The fermentation was performed at a temperature of 37° C., an air flow rate of 5 L/min, dissolved oxygen controlled at 30%, and a speed of revolution coupled with dissolved oxygen, between 600-1200 rpm. pH was adjusted at 7.0 with 5 M ammonia. Supplementary medium had ingredients (g/L) of: 500 g of glycerol, 15 g of peptone, 30 g of yeast extract, and 30 g of $MgSO_4.7H_2O$.

The fermentation was performed in a manner of simulated exponential fed-batch mode, and the concentration of glycerol was kept below 0.5 g/L, the yield of acetic acid was kept below 0.2 g/L, and average feeding rate was 20 ml/h throughout the fermentation.

After 9 h of the fermentation, 2 ml of the strain solution was sampled every 4 h, and centrifuged at 14000 rpm for 3 min, washed with sterilized water, with supernatants discarded, and stored in a refrigerator at −20° C. Prior to use, the sample was added with 1 ml of acetone, and extracted at 55° C. in dark for 15 min, and centrifuged at 14000 rpm for 10 min Supernatant thereof was used to determine the content of β-carotene with HPLC (Agilent Technologies high performance liquid chromatograph 1260 Infinity).

TABLE 2

Combined modification of TCA function module and PPP function module of recombinant E. coli CAR001 and improvement of β-carotene production

| Strain | Genetic background | $OD_{600}$ | Dry weight (g/L) | β-carotene content (mg/L) | β-carotene yield (mg/g) | Increased folds |
|---|---|---|---|---|---|---|
| CAR001 | | 4.31 ± 0.01 | 1.39 ± 0.01 | 25.67 ± 0.01 | 18.40 ± 0.01 | 0 |
| CAR002 | CAR001, SucAB46 | 4.35 ± 0.03 | 1.40 ± 0.03 | 33.40 ± 0.03 | 23.77 ± 0.03 | 29% |
| CAR003 | CAR001, SucAB46-TalB46 | 4.06 ± 0.04 | 1.31 ± 0.04 | 32.17 ± 0.06 | 24.54 ± 0.06 | 33% |
| CAR004 | CAR001, SucAB46-Sdh46 | 4.38 ± 0.03 | 1.42 ± 0.03 | 39.34 ± 0.04 | 27.78 ± 0.04 | 51% |
| CAR005 | CAR001, SucAB46-Sdh46-TalB46 | 4.01 ± 0.00 | 1.29 ± 0.00 | 39.03 ± 0.02 | 30.17 ± 0.02 | 64% |

EXAMPLE 10

High-Density Fermentation of Recombinant E. coli CAR005

High-density fermentation of recombinant E. coli CAR005 was performed in a 7 L fermentation tank (Labfors 4; Infors Biotechnoligy Co. Ltd.), by a method as below: a single colony was picked into 4 ml of a LB culture medium in a tube, and cultivated at 30° C., 250 rpm overnight; then, an amount of 1% of the strain solution, i.e. 300 μl of the strain solution, from the tube was inoculated into 50 ml culture medium in a 250 ml Tri Flask, and after culture at 37° C., 250 rpm for 24 h, the strain solution was namely the seed for the high-density fermentation. The high-density fermentation thereof was performed with a synthetic culture medium. A 7 L fermentation tank was charged with 3 L of the fermentation culture medium, and 300 ml of the seed solution.

The fermentation culture medium (g/L) had ingredients of 10 g of glycerol, 1.7 g of citric acid, 10.5 g of $KH_2PO_4.3H_2O$, 6 g of $(NH_4)_2HPO_4$, 3.44 g of $MgSO_4.7H_2O$, and 10 ml of a trace element solution. The trace element solution had ingredients (g/L) of: 10 g of $FeSO_4.7H_2O$, 5.25 g of $ZnSO_4.7H_2O$, 3.0 g of $CuSO_4.5H_2O$, 0.5 g of $MnSO_4.4H_2O$, 0.23 g of $Na_2B_4O_7.10H_2O$, 2.0 g of $CaCl_2$, and 0.1 g of $(NH_4)_6MO_7O_{24}$.

Standard β-carotene (Sigma, US (Cat. No. C4582)) was remained at −80° C., and was used to determine a standard curve immediately after received; when β-carotene was extracted from the supernatant, its content was immediately measured with HPLC (by a method as above), to demonstrate the containment of β-carotene (the supernatant exhibited yellow, but strain became white from yellow after the extraction with acetone; in the HPLC assay, the sample had an appearance time of β-carotene identical with that of the standard (an appearance time of 17.2 min), confirming the containment of β-carotene).

Figure 5:
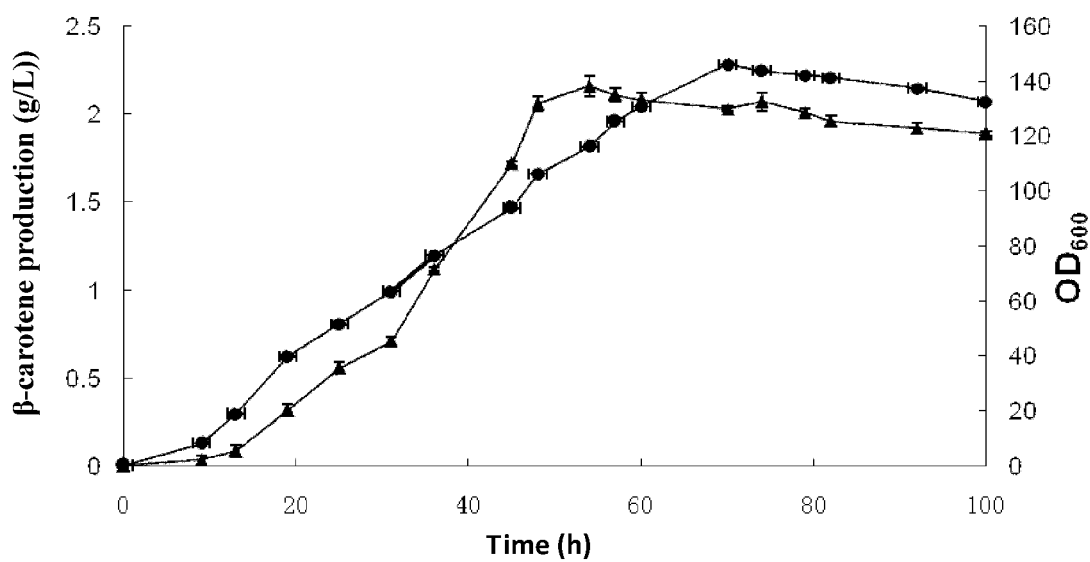
FIG. 5 shows production of β-carotene by high-density fermentation of recombinant *E. coli* CAR005.

The fermentation results were shown in FIG. 5. The high-density fermentation was in a period of 100 h, wherein the cells entered a stable phase at 70 h, and finally had $OD_{600}$ of 146, and a dry weight of 47.16 g/L DCW. The yield of β-carotene kept increasing in first 56 h, with a maximum yield of 2.16 g/L, and a maximum yield per cell of 60 mg/g DCW.

EXAMPLE 11

Deletion of crtXY Gene of Recombinant E. coli CAR001 and Production of Lycopene

1. Deletion of crtXY Gene of Recombinant E. coli CAR001 and Construction of Recombinant Strain LYC001

Recombinant strain LYC001 was obtained by deletion of the β-carotene cyclase gene crtX and lycopene β-cyclase gene crtY from β-carotene synthesis gene cluster of recombinant *E. coli* CAR001, via homologous recombination, specifically as below:

Procedures in a way as Example 1, part II:

Step 1: amplifying 4000 bp DNA fragment I with the plasmid DNA of pLOI4162 as a template, and primers CrtE-taa-cat-f/CrtI-atg-cat-r, the fragment being DNA fragment I comprising chloromycetin gene and levansucrose transferase gene;

```
CrtE-taa-cat-f:
ACCATTTGTTCAGGCCTGGTTTGAGAAAAAACTCGCTGCCGTCAGTTA

ATGTGACGGAAGATCACTTCGCA

CrtI-atg-cat-r:
GCCAGAGCCAGACCACCAAAGCCTGCGCCAATTACTGTAGTTCTATTCAT

TTATTTGTTAACTGTTAATTGTCCT
```

Step 2: electrotransforming DNA fragment I obtained in Step 1 into *E. coli* CAR001 with pKD46, to obtain strain JZ001;

Step 3: amplifying with the plasmid DNA of pTrc99A-M-crt as a template, and primers crtE-r/crtI-RBS-F, to obtain an about 7000 bp PCR product:

```
CrtE-r: TTAACTGACGGCAGCGAGTT

CrtI-RBS-F: CTAAGGAGATATACCATGAATAGAACTACAGTAATTG

GCGC;
```

Step 4: phosphorylating and self-linking the about 7000 bp PCR product obtained by the amplification in Step 3, to obtain plasmid pTrc99A-M-crtEIB for use in second homologous recombination, the plasmid being a recombinant vector comprising the lycopene synthesis gene cluster, which was a gene cluster consisting of geranylgeranyl diphosphate synthase gene crtE, phytoene desaturase gene crtI and phytoene synthase gene crtB;

Step 5: amplifying with the plasmid DNA of pTrc99A-M-crtEIB as a template, and primers crtE-f/crtI-484-r to obtain an about 1500 bp DNA fragment II:

```
CrtE-f: atgatgacggtctgtgcagaa crtI-484-r: TTAACTGACGGCAGCGAGTT;
```

Step 6: electrotransforming the about 1500 bp DNA fragment II obtained in Step 5 into JZ001 with pKD46 plasmid, to obtain a strain having crtXY gene deleted, which was designated as LYC001.

2. Production of Lycopene by Fermentation of Recombinant *E. coli* LYC001

A single colony of recombinant *E. coli* LYC001 was picked into 4 ml of LB culture medium in a tube, and cultivated at 37° C., 250 rpm overnight; then, an amount of 1% of the overnight cultivated seed solution was inoculated to 10 ml of a LB culture medium in a 100 ml Tri Flask, and cultivated at 37° C., 250 rpm in dark for 24 h, after which samples were taken to determine the lycopene yield, in triplicate for each sample.

Determination of lycopene standard curve: standard of lycopene (P/N: L 9 8 7 9) was supplied by Sigma, and used for the determination of the standard curve immediately after received; the filter used for filtration was 0.45 μm millipore filter (Millpor); acetone, methanol, dichloromethane, petroleum ether, acetonitrile were chromatographic pure agents, supplied by Merk.

50 mg of lycopene standard was precisely weighted and added to 1 ml of dichloromethane to dissolve, and then transferred to a 250 ml brown volumetric flask, and made up with petroleum ether to 250 ml, to formulate a 200 μg/ml stock solution (stored in a refrigerator at −80° C.). When used, it was serially diluted (2×, 4×, 8×, 16×, 32×) with acetone, and filtered into HPLC vials, to subject to HPLC detection (with a Symmetry C18 column (4.6×250 mm, 5 μm); column temperature: 30° C.; mobile phase: methanol:acetonitrile:dichloromethane=21:21:8; injection volume: 20 μl; injection time: 20 min; DAD light detection; and detection wavelength of 480 nm), and through a relation between standard peak area and lycopene concentration, to obtain a standard curve of lycopene.

Step 2: a single colony of recombinant *E. coli* LYC001 was picked into 4 ml of LB culture medium in a tube, and cultivated at 37° C., 250 rpm overnight; then, an amount of 1% of the overnight cultivated seed solution was inoculated to 10 ml of a LB culture medium in a 100 ml Tri Flask, and cultivated at 37° C., 250 rpm in dark for 24 h, after which samples were taken to determine lycopene yield, in triplicate for each sample.

After lycopene was extracted from supernatant, its content was immediately measured with HPLC; supernatant exhibited red, but the strain became white from red after extraction with acetone. In the HPLC assay, the samples had an appearance time of lycopene identical with that of the standard (an appearance time of 11.3 min).

The results are seen in Table 4. The lycopene yield of LYC001 was up to 10.49 mg/L, and the content of LYC001 was up to 6.52 mg/g dry cell weight.

EXAMPLE 12

Improvement of Expression Strength of α-Ketoglutarate Dehydrogenase Gene of Recombinant *E. coli* LYC001

1. Improvement of the Expression Strength of α-Ketoglutarate Dehydrogenase Gene of Recombinant *E. coli* LYC001 and Construction of Recombinant Strain LYC002

Recombinant strain LYC002 was obtained from LYC001 with original regulatory part (SEQ ID NO: 15) of sucAB gene replaced with artificial regulatory part M1-46 (SEQ ID NO: 14).

A specific method is as blow (two-step homologous recombination):

Step 1: as Step 1 of part 1 in Example 2, except that the starting vector was pLOI4162 plasmid, the amplification primers were SucAB-cat-up/SucAB-cat-down, an about 3400 bp DNA fragment I was obtained; and the strain to be transformed was recombinant *E. coli* LYC001; an intermediate positive clone was obtained.

Step 2: as Step 2 of part 1 in Example 2, except that the starting strain was a recombinant strain M1-46, the amplification primers were SucAB-up-P/SucAB-RBS-down, an about 200 bp DNA fragment II was obtained; the strain to be transformed was the intermediate positive clone got in step 1. Recombinant *E. coli* LYC002 was obtained.

The primers for the amplification in Step 1 were:

```
SucAB-cat-up:
GGTAGTATCCACGGCGAAGTAAGCATAAAAAAGATGCTTAAGGGATCACG

TGTGACGGAAGATCACTTCGCA

SucAB-cat-down:
CCAGAGAGGTAAGAAGAGTCCAACCAGGCTTTCAAAGCGCTGTTCTGCAT

TTATTTGTTAACTGTTAATTGTCCT
```

The primers for the amplification in Step 2 were SucAB-up-P/SucAB-RBS-down with sequences of:

```
SucAB-up-P: GGTAGTATCCACGGCGAAGTAAGCATAAAA
```

The PCR identification primers in above two steps had sequences of (an amplified fragment of about 400 bp was positive):

```
ApI-up: TTATCTCTGGCGGTGTTGAC sucAB-r: GAAATATTCACGCGTTTGAG
```

After verifying the right clones by sequencing, the strain having the regulatory part sucAB gene of LYC001 replaced with artificial regulatory part M1-46 was designated as recombinant E. coli LYC002.

2. Production of Lycopene by Recombinant E. coli LYC002

A Fermentation culturing of recombinant E. coli LYC002 was performed in the way of Example 11, to determine lycopene yield. The results are seen in Table 4. 10.67 mg/g lycopene was produced by recombinant E. coli LYC002; after the regulation of sucAB, lycopene yield was improved over LYC001 by 64%.

EXAMPLE 13

Combined Regulation of Expression Intensities of α-Ketoglutarate Dehydrogenase Gene and Transaldolase Gene of Recombinant E. coli LYC001

1. Combined Regulation of the Expression Intensities of α-Ketoglutarate Dehydrogenase Gene and Transaldolase Gene of Recombinant E. coli LYC001

Recombinant E. coli LYC003 was LYC002 having original regulatory part (SEQ ID NO: 17) of talB gene replaced with artificial regulatory part M1-46.

Detailed method was as below (two-step homologous recombination):

Step 1: as Step 1 of part 1 in Example 2, except that the starting vector was pLOI4162 plasmid, the amplification primers were talB-cat-up/talB-cat-down, an about 3400 bp DNA fragment I was obtained; and the strain to be transformed was recombinant E. coli LYC002; an intermediate positive clone was obtained.

Step 2: as Step 2 of part 1 in Example 2, except that the starting strain was recombinant strain M1-46, the amplification primers were talB-up-P/talB-RBS-down, an about 200 bp DNA fragment II was obtained; and the strain to be transformed was the intermediate positive clone got in step 1. Recombinant E. coli LYC003 was obtained.

The primers for the amplification in Step 1 were:

```
talB-cat-up:
AGTCTCGCCTGGCGATAACCGTCTTGTCGGCGGTTGCGCTGACGTTGCG

TCGTGTGTGACGGAAGATCACTTCGCA talB-cat-down:
TCATGATAGTATTTCTCTTTAAACAGCTTGTTAGGGGGATGTAACCGGTC

TGCTTATTTGTTAACTGTTAATTGTCCT
```

The primers for the amplification in Step 2 were talB-up-P/talB-RBS-down having sequences of:

```
talB-up-P:
AGTCTCGCCTGGCGATAACCGTCTTGTCGGCGGTTGCGCTGACGTTGCG

TCGTGTTATCTCTGGCGGTGTTGAC talB-RBS-down:
AGTGTCGGCCACTACGGTGGTGTACTGACGAAGGGAGGTCAATTTGTCC

GTCATAGCTGTTTCCTGGTT
```

In above two steps, the identification primers were talB-up/talB-down having sequences of (the correct PCR fragment was about 900 bp):

```
talB-up: CGGATGTAGCGAAACTGCAC talB-down: GACGCTTCGGTGTCATAGGAAAG.
```

After verifying the right clones by sequencing, the strains having original regulatory part of talB gene of LYC002 replaced with artificial regulatory part M1-46 were designated as recombinant E. coli LYC003, respectively.

2. Production of Lycopene by Recombinant E. coli LYC003

A Fermentation culturing of recombinant E. coli LYC003 was preformed in the way of Example 11, to determine lycopene yield.

The results are seen in Table 4. 11.03 mg/g lycopene was produced by recombinant E. coli LYC003; after the combined regulation of sucAB and talB, the lycopene yield was improved over LYC001 by 70%.

EXAMPLE 14

Combined Regulation of Expression Intensities of α-Ketoglutarate Dehydrogenase Gene, Transaldolase Gene and Succinate Dehydrogenase Gene of Recombinant E. coli LYC001

I. Combined Regulation of the Expression Intensities of α-Ketoglutarate Dehydrogenase Gene, Transaldolase Gene and Succinate Dehydrogenase Gene of Recombinant E. coli LYC001

1. Construction of Recombinant E. coli LYC005

Recombinant E. coli LYC005 was recombinant E. coli LYC003 having original regulatory part (SEQ ID NO: 16) of sdhABCD gene replaced with artificial regulatory part M1-46.

Detailed method was as below (two-step homologous recombination):

Step 1: as Step 1 of part 1 in Example 2, except that the starting vector was pLOI4162 plasmid, the amplification primers were SdhABCD-cat-up/SdhABCD-cat-down, an about 3400 bp DNA fragment I was obtained; and the strain to be transformed was recombinant E. coli LYC002; an intermediate positive clone was obtained.

Step 2: as Step 2 of part 1 in Example 2, except that the starting strain was recombinant strain M1-46, the amplification primers were SdhABCD-up-P/SdhABCD-RBS-down, an about 200 bp DNA fragment II was obtained; the strain to be transformed was the intermediate positive clone got in step 1. Recombinant *E. coli* LYC005 was obtained.

Step 1 amplification primers:

```
SdhABCD-cat-up:
ACTTTGTTGAATGATTGTCAAATTAGATGATTAAAAATTAAATAAATGTT

TGTGACGGAAGATCACTTCGCA

SdhABCD-cat-down:
TTAACAGGTCTTTGTTTTTTCACATTTCTTATCATGAATAACGCCCACAT

TTATTTGTTAACTGTTAATTGTCCT
```

The primers for the amplification in Step 2 were SdhABCD-up-P/SdhABCD-RBS-down having sequences of:

```
SdhABCD-up-P:
ACTTTGTTGAATGATTGTCAAATTAGATGATTAAAAATTAAATAAATGTT

TTATCTCTGGCGGTGTTGAC

SdhABCD-RBS-down:
TTAACAGGTCTTTGTTTTTTCACATTTCTTATCATGAATAACGCCCACAT

AGCTGTTTCCTGGTT
```

The identification primers ApI-up and sdhABCD-r in above two steps (an obtained fragment of about 400 bp was positive) were:

```
ApI-up: TTATCTCTGGCGGTGTTGAC sdhABCD-r: AATTTGACGAAGAAGCTGC.
```

After verifying the right clones by sequencing, the strain, having the regulatory part of sdhABCD gene of LYC003 replaced with artificial regulatory part M1-46, was designated as recombinant *E. coli* LYC005.

2. Production by Recombinant *E. coli* LYC005

A Fermentation culturing of recombinant *E. coli* LYC005 was performed in the way of Example 11, to determine lycopene yield.

The results are seen in Table 3. 11.53 mg/g of lycopene was produced by recombinant *E. coli* LYC005; after the combined regulation of genes sucAB, talB and sdhABCD, the lycopene yield was improved over LYC001 by 76%.

EXAMPLE 15

High-Density Fermentation of Recombinant *E. coli* LYC005

High-density fermentation of recombinant *E. coli* LYC005 was performed in a 7 L fermentation tank (Labfors 4; Infors Biotechnoligy Co. Ltd.), by a method as below: single colonies were picked into 4 ml of a LB culture medium in a tube, and cultivated at 30° C., 250 rpm overnight; then, an amount of 1% of the strain solution, i.e. 300 μl of the strain solution, in the tube was inoculated to 50 ml of a LB culture medium in a 250 ml Tri Flask, and cultivated at 37° C., 250 rpm for 12 h, the resulting strain solution being the seed for high-density fermentation. The high-density fermentation thereof was performed using a synthetic culture medium. A 7 L fermentation tank was charged with 3 L of the fermentation culture medium, and 300 ml of the seed solution.

The fermentation culture medium (g/L) had ingredients of 10 g of glycerol, 1.7 g of citric acid, 10.5 g of $KH_2PO_4.3H_2O$, 6 g of $(NH_4)_2HPO_4$, 3.44 g of $MgSO_4.7H_2O$, and 10 ml of a trace element solution. The trace element solution had ingredients (g/L) of: 10 g of $FeSO_4.7H_2O$, 5.25 g of $ZnSO_4.7H_2O$, 3.0 g of $CuSO_4.5H_2O$, 0.5 g of $MnSO_4.4H_2O$, 0.23 g of $Na_2B_4O_7.10H_2O$, 2.0 g of $CaCl_2$, and 0.1 g of $(NH_4)_6MO_7O_{24}$.

The fermentation was performed at a temperature of 30° C., an air flow rate of 4 L/min, and dissolved oxygen controlled at 30%. In order to control dissolved oxygen at 30%, it was required that the speed of revolution was coupled with the dissolved oxygen, with speed of revolution maintained at 400-1200 rpm, and constantly maintained at 1200 rpm after the dissolved oxygen was recovered (the initial carbon source was exhausted). pH was controlled at 7.0 with 5 M ammonia. A supplemented medium (g/L) had ingredients of: 500 g of glycerol, 15 g of peptone, 30 g of yeast extract, and 30 g of $MgSO_4.7H_2O$.

The fermentation was performed in a way of simulated exponential fed-batch mode, and throughout the fermentation the concentration of glycerol was kept below 0.5 g/L, the yield of acetic acid was kept below 0.2 g/L, and the average feed rate was 18 ml/h. After 10 h of fermentation, 2 ml of the strain solution was sampled every 6 h, centrifuged at 14000 rpm for 3 min, washed with sterilized water, with supernatant discarded, and stored in a refrigerator at −20° C. Prior to the content measurement, the samples were added with 1 ml of acetone, extracted at 55° C. in dark for 15 min, and centrifuged at 14000 rpm for 10 min, and the supernatant was taken for measure the content of lycopene

TABLE 3

Combined engineering of TCA function module and PPP function module of recombinant *E. coli* LYC001 and improved production of β-carotene

| Strain | Genetic background | $OD_{600}$ | Dry weight (g/L) | Lycopene content (mg/L)[a] | Lycopene yield (mg/g) | Increased folds |
|---|---|---|---|---|---|---|
| LYC001 | | 4.25 ± 0.22 | 1.61 ± 0.12 | 10.49 ± 0.52 | 6.52 ± 0.11 | 0 |
| LYC002 | LYC001, SucAB46 | 3.79 ± 0.04 | 1.44 ± 0.02 | 15.36 ± 0.11 | 10.67 ± 0.03 | 64% |
| LYC003 | LYC001, SucAB46-TalB46 | 3.79 ± 0.08 | 1.44 ± 0.04 | 15.89 ± 0.08 | 11.03 ± 0.02 | 70% |
| LYC005 | LYC001, SucAB46-Sdh46-TalB46 | 4.34 ± 0.04 | 1.64 ± 0.02 | 18.91 ± 0.61 | 11.53 ± 0.18 | 76% | using HPLC (Agilent Technologies high performance liquid chromatograph 1260 Infinity).

Figure 6:
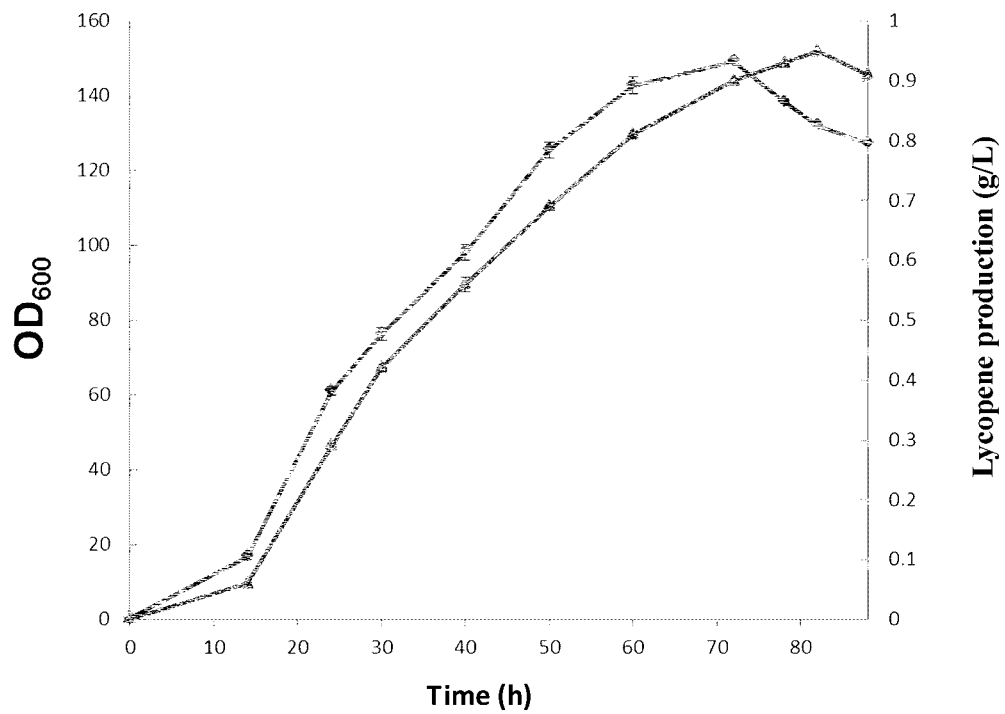
FIG. 6 shows production of lycopene by fermentation of recombinant *E. coli* LYC005.

The fermentation results were shown in FIG. 6. The high-density fermentation was in a period of 88 h, wherein the cells entered a stable phase at 72 h, and finally had $OD_{600}$ of 149, and a weight of 56.55 g/L DCW. The yield of β-carotene kept increasing in first 82 h, with a maximum yield of 0.95 g/L.

EXAMPLE 16

Improvement of Expression Strength of sucAB Gene of E. coli ATCC8739 and Improvement of β-Carotene and Lycopene I. Construct of Recombinant Strains E. coli ATCC8739 (pTrc99A-M-Crt), 8739-SucAB46 (pTrc99A-M-Crt), ATCC8739 (pTrc99A-M-crtEIB), and 8739-SucAB46 (pTrc99A-M-crtEIB)
1. Construction of Recombinant Strain 8739-SucAB46
1) Construction of Recombinant Strain 8739-SucAB46

Recombinant E. coli 8739-SucAB46 was a strain in which original regulatory part (SEQ ID NO: 15) of sucAB gene of ATCC8739 was replaced with artificial regulatory part M1-46 (SEQ ID NO: 14).

Detailed method is as below (two-step homologous recombination):

Step 1: as Step 1 of part 1 in Example 2, except that the starting vector was pLOI4162 plasmid, the amplification primers were SucAB-cat-up/SucAB-cat-down, an about 3400 bp DNA fragment I was obtained; and the strain to be transformed was ATCC8739;

Step 2: as Step 2 of part 1 in Example 2, except that the starting strain was a recombinant strain M1-46, the amplification primers were SucAB-up-P/SucAB-RBS-down, an about 200 bp DNA fragment II was obtained; and the strain to be transformed was the intermediate positive clone got in step 1. Recombinant E. coli 8739-SucAB46 was obtained.

The primers for the amplification in Step 1 were:

SucAB-cat-up: GGTAGTATCCACGGCGAAGTAAGCATAAAAAAGAT

GCTTAAGGGATCACG TGTGACGGAAGATCACTTCGCA

SucAB-cat-down: CCAGAGAGGTAAGAAGAGTCCAACCAGGCTTTCA

AAGCGC TGTTCTGCAT TTATTTGTTAACTGTTAATTGTCCT.

The primers for the amplification in Step 2 were SucAB-up-P/SucAB-RBS-down having sequences of:

SucAB-up-P: GGTAGTATCCACGGCGAAGTAAGCATAAAA sucAB-RBS-down: CCAGAGAGGTAAGAAGAGTCCAACCAGGCTTTCA

AAGCGCTGTTCTGCATAGCTGTTTCCTGGTT.

The identification primers in above two steps (an amplified fragment of about 400 bp was positive) were:

ApI-up: TTATCTCTGGCGGTGTTGAC sucAB-r: GAAATATTCACGCGTTTGAG

After verifying the right clones by sequencing, the strains having the promoter of sucAB gene of ATCC8739 was replaced with artificial regulatory part M1-46 were designated as recombinant E. coli 8739-SucAB46, respectively.

2) Enzymatic Activity Assay of α-Ketoglutarate Dehydrogenase (SucAB)

Single colonies of E. coli ATCC8739 and recombinant E. coli 8739-SucAB46 were picked into 4 ml of LB culture medium (with a final concentration of 100 μg/ml of ampicillin) in a tube, and cultivated at 30° C., 250 rpm overnight, respectively; then, an amount of 1% of the strain solution, i.e. 100 μl of the strain solution, in the tube was inoculated to 10 ml of a culture medium in a 100 ml small shaking flask, and cultivated at 30° C., 250 rpm. 30 ml of the fermented solution at mid-late of logarithmic growth was placed into a 50 ml centrifuge tube, and centrifuged at 4° C., 10000 rpm for 10 min, with supernatant discarded. After washed with 5 ml of 100 mmol/L Tris-HCl solution twice, the cells were suspended in 3 ml of 100 mmol/L Tris-HCl solution, and placed into an ice tank to be ultrasonicated for 20 min. After centrifugation at 4° C., 10000 rpm for 20 min, the supernatant was used for the enzymatic activity assay. The reaction solution for the enzymatic activity assay of α-ketoglutarate dehydrogenase had a composition shown in Table 4:

TABLE 4

Composition of the reaction solution for enzymatic activity assay of α-ketoglutarate dehydrogenase

| Final concentration | Stock concentration | Volumn (ul/ml) |
|---|---|---|
| Water | | 565 |
| 50 mM potassium phosphate (pH 8.0) | 500 mM | 100 |
| 1 mM MgCl2 | 100 mM | 10 |
| 2.6 mM cysteine hydrochloride | 26 mM | 100 |
| 2.5 mM NAD+ | 25 mM | 100 |
| 0.2 mM TPP | 40 mM | 5 |
| 0.13 mM CoA | 13 mM | 10 |
| 2 mM ketogluterate potassium | 20 mM | 100 |
| Crude extract | | 10 |

10 μl of above supernatant that had been ultrasonicated and centrifuged was added and mixed well, and placed into a colorimeter cell, and changes in $A_{340}$ were recorded. A reaction buffer solution added with 10 μl of $ddH_2O$ was the control.

The enzymatic activity unit was defined as: μmol of NADH consumed by per mg of protein per minute.

The α-ketoglutarate dehydrogenase of E. coli ATCC8739 had enzymatic activity of 0.057 U/mg protein, and the enzymatic activity of α-ketoglutarate dehydrogenase of recombinant E. coli 8739-SucAB46 of 0.12 U/mg protein. With original regulatory part of sucAB gene replaced with artificial regulatory part M1-46, the enzymatic activity of α-ketoglutarate dehydrogenase was improved by 111%.

2. E. coli ATCC8739 (pTrc99A-M-Crt), 8739-SucAB46 (pTrc99A-M-Crt), ATCC8739 (pTrc99A-M-crtEIB), 8739-SucAB46 (pTrc99A-M-crtEIB)

Plasmids pTrc99A-M-crt (which plasmid contained β-carotene synthesis gene cluster crtEXYIB) and pTrc99A-M-crtEIB (which plasmid contained lycopene synthesis gene cluster crtEIB, as constructed by a process in Example 11) were electrotransformed into ATCC8739 and 8739-SucAB46, respectively. The electrotransformation was in conditions that: firstly, competent cells of E. coli ATCC8739 and 8739-SucAB46 to be electrotransformed were prepared; 50 μl of competent cells were placed on ice, added with 1 μl of a corresponding plasmid (about 50 ng/μl), and kept to stand on ice for 2 minutes, and thereafter was transferred to a 0.2 cm Bio-Rad cuvette, and subjected to electric shock using an MicroPulser (Bio-Rad) electroporation apparatus, with an electric shock parameter of a voltage of 2.5 kv. After the electric shock, 1 ml of LB culture medium was immediately transferred to the cuvette, and lashed 5 times, and then it was transferred to a tube, and incubated at 75 rpm, 30° C. for 2 hours. 50 µl of the strain solutions were coated on a LB plate containing ampicillin, and incubated at 37° C. overnight. Thereafter, 5 positive single colonies were picked for a liquid culturing, and positive cloned plasmids were extracted for verification by digestion. The results showed that each of the plasmids was successfully transformed into a corresponding strain, to obtain E. coli ATCC8739 (pTrc99A-M-crt), 8739-SucAB46 (pTrc99A-M-crt), ATCC8739 (pTrc99A-M-crtEIB), and 8739-SucAB46 (pTrc99A-M-crtEIB).

II. Production of β-Carotene and Lycopene

Single colonies of recombinant E. coli ATCC8739 (pTrc99A-M-crt), 8739-SucAB46 (pTrc99A-M-crt), ATCC8739 (pTrc99A-M-crtEIB), and 8739-SucAB46 (pTrc99A-M-crtEIB) were picked into 4 ml of LB culture medium (with a final concentration of 100 µg/ml of ampicillin) in a tube, and cultivated at 30° C., 250 rpm overnight, respectively; then, an amount of 1% of the strain solution, i.e. 100 µl of the strain solutions, in the tubes were inoculated to 10 ml of a culture medium in a 100 ml small shaking flask, and cultivated at 30° C., 250 rpm for 24 h, respectively. Thereafter, samples were taken to determine β-carotene and lycopene yields. The β-carotene yield was determined by a method as seen in Example 1 and the lycopene yield was determined by a method as seen in Example 11.

Recombinant E. coli ATCC8739 (pTrc99A-M-crt) had a β-carotene yield of 0.58 mg/g, 8739-SucAB46 (pTrc99A-M-crt) had a β-carotene yield of 0.75 mg/g. After the regulation of sucAB, the β-carotene yield was improved by 29%.

Recombinant E. coli ATCC8739 (pTrc99A-M-crtEIB) had a lycopene yield of 0.12 mg/g, and 8739-SucAB46 (pTrc99A-M-crtEIB) had a lycopene yield of 0.38 mg/g. After the regulation of sucAB, the lycopene yield was improved by 217%.

INDUSTRIAL APPLICATION

It is confirmed from the experiments of the present invention that the present invention regulates the expression of key genes in MEK pathway using a gene expression regulating strategy different than previously used, and studies the effect thereof on the capability of β-carotene production. Several artificial regulatory parts with different intensities are used to regulate these key genes, to find optimal expression intensity strength for each of the genes. In the present invention, a plurality of recombinant strains are constructed to improve the activities of α-ketoglutarate dehydrogenase, succinate dehydrogenase and transaldolase, so as to improve the ability of a cell to synthesize NADPH and ATP, thus to improve the efficiency of the MEP pathway and the production capability of terpenoid. Particularly, the expression strength of α-ketoglutarate dehydrogenase gene sucAB was improved in E. coli by homologous recombination, so that the productions of β-carotene and lycopene may be improved.

What is claimed:

1. A recombinant *E. coli* strain 1, comprising an artificial regulatory part that has been introduced into the chromosome of a starting *E. coli* strain to replace an original regulatory part of an α-ketoglutarate dehydrogenase (sucAB) gene, wherein
the original regulatory part of the sucAB gene comprises a nucleotide sequence of SEQ ID NO: 15, the artificial regulatory part is selected from the group consisting of
(a) M1-46 having a nucleotide sequence of SEQ ID NO: 14,
(b) M1-37 having a nucleotide sequence of SEQ ID NO: 10, and
(c) M1-93 having a nucleotide sequence of SEQ ID NO: 11,
and wherein the recombinant *E. coli* strain 1 exhibits an increased α-ketoglutarate dehydrogenase enzymatic activity relative to the starting *E. coli* strain.

2. The recombinant *E. coli* strain 1 according to claim 1, wherein: the recombinant *E. coli* strain 1 is further defined as:
I) recombinant *E. coli* strain 1-1, wherein the artificial regulatory part is M1-46 having a nucleotide sequence of SEQ ID NO: 14; or
II) recombinant *E. coli* strain 1-2, wherein the artificial regulatory part is selected from the group consisting of
(a) M1-46 having a nucleotide sequence of SEQ ID NO: 14, (b) M1-37 having a nucleotide sequence of SEQ ID NO: 10, and (c) M1-93 having a nucleotide sequence of SEQ ID NO: 11, and the starting *E. coli* strain is an *E. coli* mutant A constructed by a method comprising the steps of:
(i) introducing a β-carotene synthesis gene cluster comprising a trc regulatory part into the chromosome of *E. coli* strain ATCC 8739 to obtain an intermediate *E. coli* strain;
(ii) in the intermediate *E. coli* strain obtained from step (i), replacing (a) the trc regulatory part of the β-carotene synthesis gene cluster with an artificial regulatory part M1-93, (b) an original regulatory part of an 1-deoxy-D-xylulose-5-phosphate synthase gene dxs with an artificial regulatory part M1-37, and (c) an original regulatory part of an isopentenyl diphosphate isomerase gene idi with an artificial regulatory part M1-37, wherein
the β-carotene synthesis gene cluster is a gene cluster consisting of a geranyl-geranyl diphosphate synthase gene crtE, a β-carotene cyclase gene crtX, a lycopene β-cyclase gene crtY, a phytoene desaturase gene crtI and a phytoene synthase gene crtB,
the original regulatory part of the 1-deoxy-D-xylulose-5-phosphate synthase gene dxs has a nucleotide sequence of SEQ ID NO:8, the original regulatory part of the isopentenyl diphosphate isomerase gene idi has a nucleotide sequence of SEQ ID NO:12, and the β-carotene synthesis gene cluster is inserted at site ldhA of the chromosome of E. coli strain ATCC 8739; or (III) recombinant E. coli strain 1-3, wherein the starting E. coli strain is an E. coli mutant B in which the original regulatory part of α-ketoglutarate dehydrogenase gene sucAB has been replaced by the artificial regulatory part M1-46, wherein the E. coli mutant B is constructed by a method comprising a step of deleting a β-carotene cyclase gene crtX and a lycopene β-cyclase gene crtY of the carotene synthesis gene cluster of the recombinant E. coli strain 1-2 of (II).

3. The recombinant E. coli strain 1-1 according to claim 2, wherein the E. coli strain 1-1 is further defined as:

(I) recombinant E. coli strain 1-1-A which is constructed by a method comprising introducing a β-carotene synthesis gene cluster into the recombinant strain 1-1, wherein the introducing of the β-carotene synthesis gene cluster into the recombinant strain 1-1 comprises introducing a recombinant vector comprising the β-carotene synthesis gene cluster into the recombinant E. coli strain 1-1; or (II) recombinant E. coli strain 1-1-B which is constructed by a method comprising introducing a lycopene synthesis gene cluster into the recombinant E. coli strain 1-1, wherein the introducing of the lycopene synthesis gene cluster comprises introducing a recombinant vector comprising the lycopene synthesis gene cluster into the recombinant E. coli strain 1-1; and wherein the lycopene synthesis gene cluster is a gene cluster consisting of a geranyl-geranyl diphosphate synthase gene crtE, a phytoene desaturase gene crtI and a phytoene synthase gene crtB.

4. A recombinant E. coli strain 2, which is constructed by a method comprising the steps of:

I) introducing a β-carotene synthesis gene cluster comprising a trc regulatory part into the chromosome of a starting E. coli strain, to obtain an intermediate E. coli strain;

II) in the intermediate E. coli strain obtained from step (I), replacing (a) an trc regulatory part of an β-carotene synthesis gene cluster with an artificial regulatory part M1-93,(b) an original regulatory part of an 1-deoxy-D-xylulose-5-phosphate synthase gene dxs with an artificial regulatory part M1-37, and (c) an original regulatory part of an isopentenyl diphosphate isomerase gene idi with an artificial regulatory part M1-46, wherein the β-carotene synthesis gene cluster is a gene cluster consisting of a geranyl-geranyl diphosphate synthase gene crtE, a β-carotene cyclase gene crtX, a lycopene β-cyclase gene crtY, a phytoene desaturase gene crtI, and a phytoene synthase gene crtB;

the trc regulatory part of the β-carotene synthesis gene cluster has a nucleotide sequence of SEQ ID NO: 6;

the artificial regulatory part M1-12 has a nucleotide sequence of SEQ ID NO: 7;

the original regulatory part of the 1-deoxy-D-xylulose-5-phosphate synthase gene dxs has a nucleotide sequence of SEQ ID NO:8;

the artificial regulatory part M1-37has a nucleotide sequence of SEQ ID NO: 10in the sequence listing;

the original regulatory part of the isopentenyl diphosphate isomerase gene idi has a nucleotide sequence of SEQ ID NO:12;

the artificial regulatory part M1-46has a nucleotide sequence of SEQ ID NO: 14;

the artificial regulatory part M1-93has a nucleotide sequence of SEQ ID NO: 11; and the starting strain is E. coli strain ATCC 8739.

5. The recombinant E. coli strain 2according to claim 4, wherein the β-carotene synthesis gene cluster is introduced into the starting E. coli strain at site ldhA of its chromosome.

6. A recombinant E. coli strain 3, wherein each of the original regulatory part of α-ketoglutarate dehydrogenase gene sucAB, the original regulatory part of succinate dehydrogenase gene sdhABCD, and/or the original regulatory part of transaldolase gene talB of the recombinant strain 2 according to claim 4 has been replaced with an artificial regulatory part M1-46, wherein the original regulatory part of α-ketoglutarate dehydrogenase gene sucAB has a nucleotide sequence of SEQ ID NO: 15;

the original regulatory part of succinate dehydrogenase gene sdhABCD has a nucleotide sequence of SEQ ID NO: 16;

the original regulatory part of transaldolase gene talB has a nucleotide sequence of SEQ ID NO: 17; and the artificial regulatory part M1-46 has a nucleotide sequence of SEQ ID NO: 14as set forth in the sequence listing.

7. The recombinant E. coli strain 3 according to claim 6, wherein the recombinant strain 3 is further defined as:

(I) recombinant strain 3-1, wherein each of the original regulatory parts of α-ketoglutarate dehydrogenase gene SucAB, succinate dehydrogenase gene sdhABCD and transaldolase gene talB of the recombinant strain 2 according to claim 4 has been replaced with an artificial regulatory part M1-46; or (II) recombinant strain 3-2, wherein the original regulatory part of α-ketoglutarate dehydrogenase gene sucAB of recombinant strain 2 according to claim 4 has been replaced with an artificial regulatory part M1-462; or (III) recombinant strain 3-3, wherein each of the original regulatory part of α-ketoglutarate dehydrogenase gene sucAB and the original regulatory part of succinate dehydrogenase gene sdhABCD of the recombinant strain 2 according to claim 4 has been replaced with an artificial regulatory part M1-46; or (IV) recombinant strain 3-4, wherein g each of the original regulatory part of α-ketoglutarate dehydrogenase gene sucAB and the original regulatory part of transaldolase gene talB of the recombinant strain 2 according to claim 4 has been replaced with an artificial regulatory part M1-46.

8. A recombinant strain 4, wherein the β-carotene cyclase gene crtX and the lycopene β-cyclase gene crtY of the β-carotene synthesis gene cluster of the recombinant strain 2 according to claim 4 has been deleted.

9. A recombinant strain 5, wherein the original regulatory parts of α-ketoglutarate dehydrogenase gene sucAB, transaldolase gene talB and/or succinate dehydrogenase gene sdhABCD of recombinant strain 4 has been replaced with an artificial regulatory part M1-46, wherein the recombinant strain 5 is further defined as (I) recombinant strain 5-1, wherein the original regulatory part of α-ketoglutarate dehydrogenase gene sucAB of the recombinant strain 4 has been replaced with an artificial regulatory part M1-46; or (II) recombinant strain 5-2, wherein is constructed by a method comprising a step of: replacing each of the original regulatory parts of α-ketoglutarate dehydrogenase gene sucAB and transaldolase gene talB of the recombinant strain 4 has been replaced with an artificial regulatory part M1-46; or (III) recombinant strain 5-3, wherein is particularly constructed by a method comprising a step of: replacing each of the original regulatory parts of α-ketoglutarate dehydrogenase gene sucAB, succinate dehydrogenase gene sdhABCD and transaldolase gene talB of the recombinant strain 4 has been replaced with an artificial regulatory part M1-46; wherein the original regulatory part of the α-ketoglutarate dehydrogenase gene sucAB has a nucleotide sequence of SEQ ID NO: 15;

the original regulatory part of the transaldolase gene talB has a nucleotide sequence of SEQ ID NO: 17;

the original regulatory part of the succinate dehydrogenase gene sdhABCD has a nucleotide sequence of SEQ ID NO: 16; and the artificial regulatory part M1-46has a nucleotide sequence of SEQ ID NO: 14.

10. A method of producing lycopene and/or β-carotene comprising:

culturing cells of a recombinant *E. coli* strain according to any one of claims 4, 6, and 9;

harvesting the cultured cells; and producing lycopene and/or β-carotene from said harvested cells.

* * * * *